(12) United States Patent
Teeslink et al.

(10) Patent No.: US 8,262,611 B2
(45) Date of Patent: *Sep. 11, 2012

(54) OCCLUSION PERFUSION CATHETER

(75) Inventors: C. Rex Teeslink, Augusta, GA (US);
Dirk V. Hoyns, Jackson, GA (US)

(73) Assignee: Advanced Catheter Therapies, Inc, Chattanooga, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/228,922

(22) Filed: Sep. 9, 2011

(65) Prior Publication Data
US 2012/0016294 A1 Jan. 19, 2012

Related U.S. Application Data

(63) Continuation of application No. 12/611,796, filed on Nov. 3, 2009, now Pat. No. 8,088,103.

(60) Provisional application No. 61/110,744, filed on Nov. 3, 2008.

(51) Int. Cl.
*A61M 25/00* (2006.01)

(52) U.S. Cl. .............. 604/101.03; 604/101.01

(58) Field of Classification Search ............ 604/96.01, 604/99.01, 99.02, 101.01, 101.03, 101.05, 604/101.06, 102.02, 919
See application file for complete search history.

(56) References Cited

U.S. PATENT DOCUMENTS

| | | | | |
|---|---|---|---|---|
| 4,777,951 A | * | 10/1988 | Cribier et al. | 606/194 |
| 5,439,446 A | * | 8/1995 | Barry | 604/103.01 |
| 5,512,045 A | | 4/1996 | Gurchumelidze | |
| 5,662,609 A | * | 9/1997 | Slepian | 604/101.03 |
| 5,921,971 A | | 7/1999 | Agro | |
| 6,152,909 A | * | 11/2000 | Bagaoisan et al. | 604/523 |
| 6,575,932 B1 | | 6/2003 | O'Brien | |
| 6,997,898 B2 | | 2/2006 | Forman | |
| 7,320,676 B2 | | 1/2008 | Miesel | |
| 8,088,103 B2 | * | 1/2012 | Teeslink et al. | 604/101.03 |
| 2002/0026145 A1 | * | 2/2002 | Bagaoisan et al. | 604/96.01 |
| 2005/0015048 A1 | | 1/2005 | Chiu | |
| 2005/0240147 A1 | | 10/2005 | Makower | |
| 2005/0267407 A1 | | 12/2005 | Goldman | |
| 2006/0074399 A1 | | 4/2006 | Bates | |
| 2007/0078433 A1 | | 4/2007 | Schwager | |
| 2008/0208118 A1 | | 8/2008 | Goldman | |
| 2009/0182227 A1 | | 7/2009 | Goldman | |

OTHER PUBLICATIONS

"International Search Report" from counterpart application No. PCT/US09/63168, mailed Jun. 11, 2010 (9 pages).
Acrostak, "Genie(TM) by Acrostak", available at http://www.acrostak.com/pdf/genie.pdf.
Kahn, Jason, "Novel Strategy Delivers Paclitaxel Directly to Vessel Wall," TCTMD.com, Jul. 27, 2009.

* cited by examiner

*Primary Examiner* — Laura Bouchelle
(74) *Attorney, Agent, or Firm* — Baker Donelson Bearman Caldwell & Berkowitz, PC

(57) ABSTRACT

Catheters for occluding, visualizing, irrigating, evacuating, and delivering agents to a treatment area are disclosed. The catheters comprise a catheter body comprising five lumens, first and second occlusion balloons coupled to the catheter body, an optional space-occupying balloon coupled to the catheter body and disposed between the first and second occlusion balloons, and an optional visualization means that enables visualization between the first and second occlusion balloons. Methods for using these catheters are also disclosed. A method comprises inflating the first and second occlusion balloons, inflating the space-occupying balloon, allowing fluid to exit via an evacuation lumen, optionally irrigating or aspirating to facilitate fluid exit via said lumen, and delivering an agent to a treatment area via the agent lumen.

19 Claims, 14 Drawing Sheets

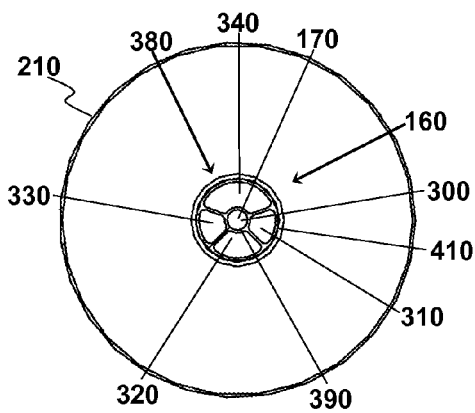
FIG. 3
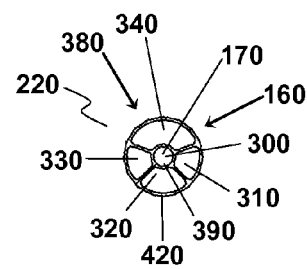
FIG. 4
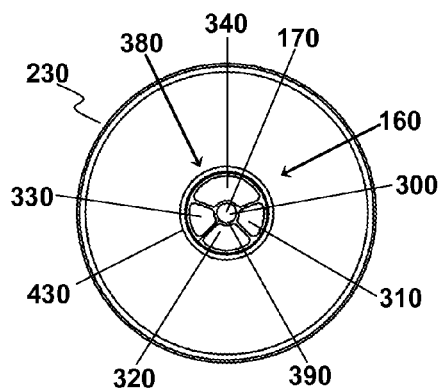
FIG. 5
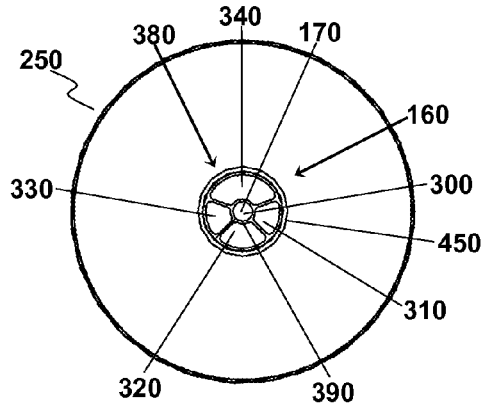
FIG. 7
FIG. 6

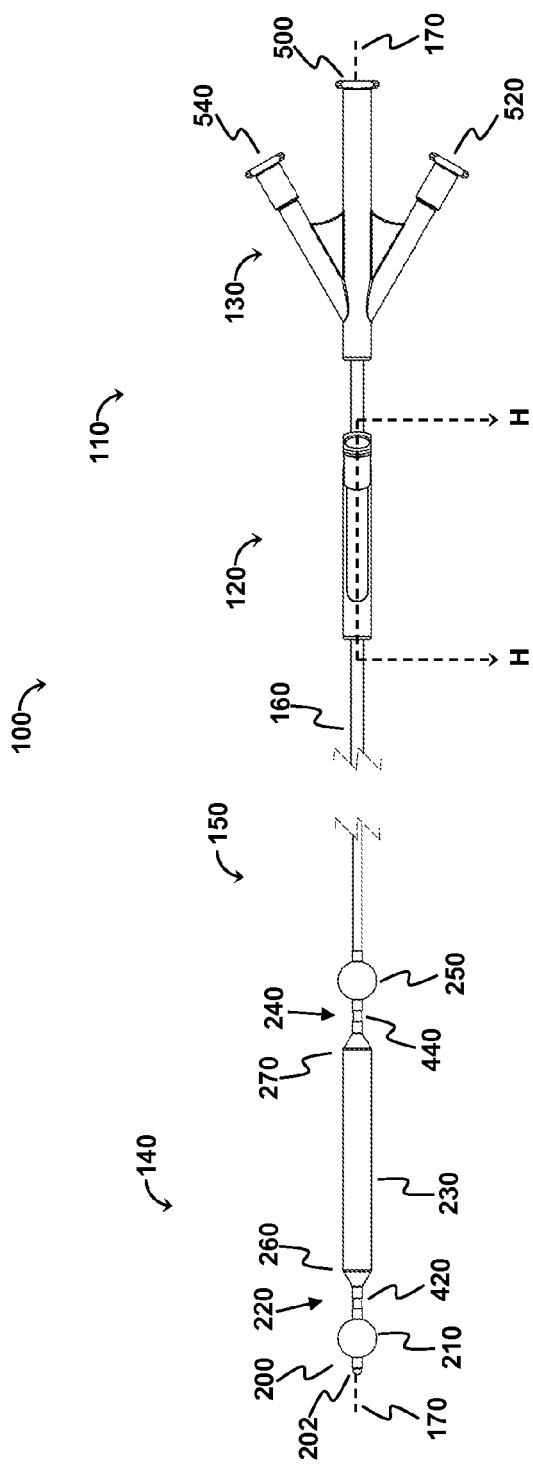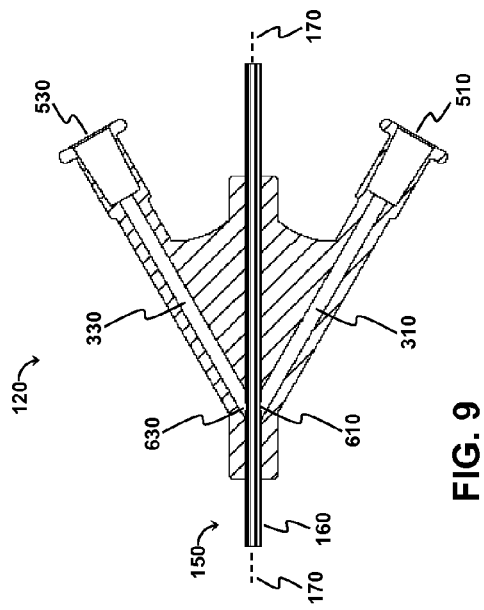
FIG. 8
FIG. 9

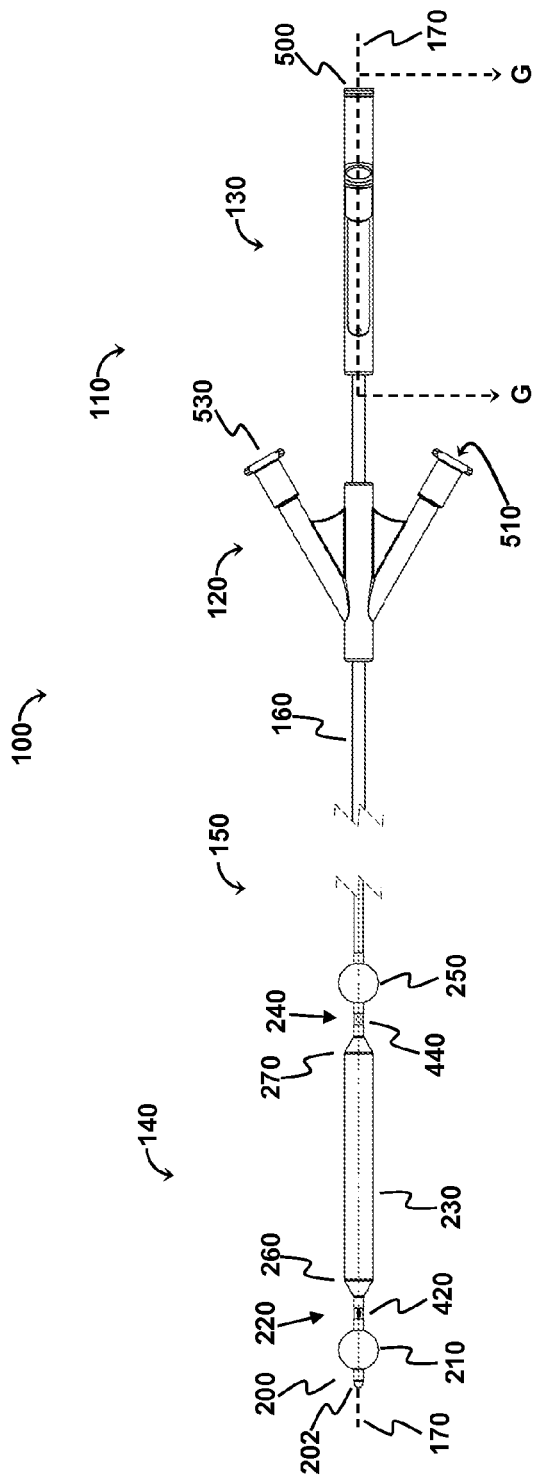
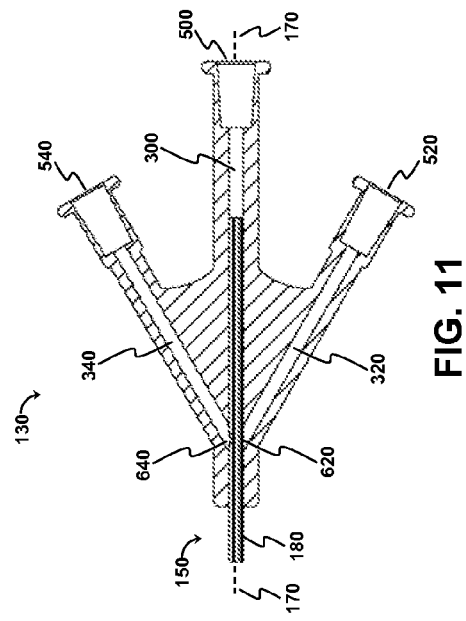
FIG. 10
FIG. 11

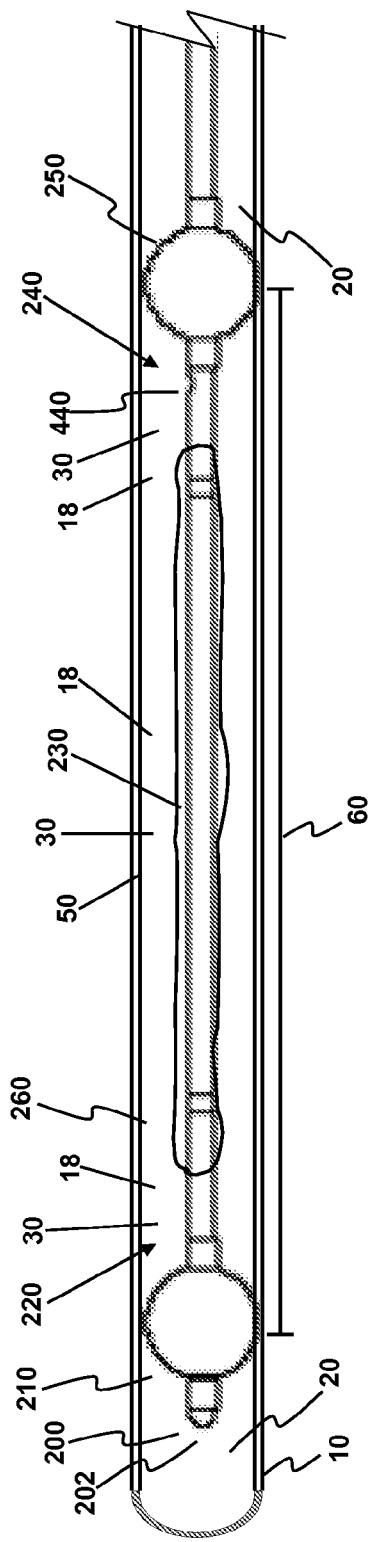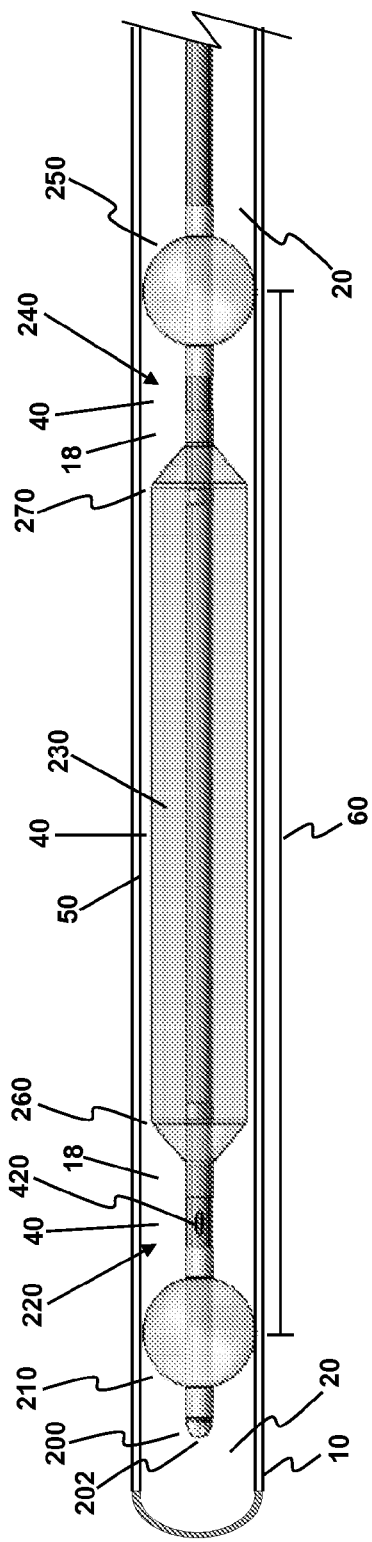
FIG. 12A
FIG. 12B

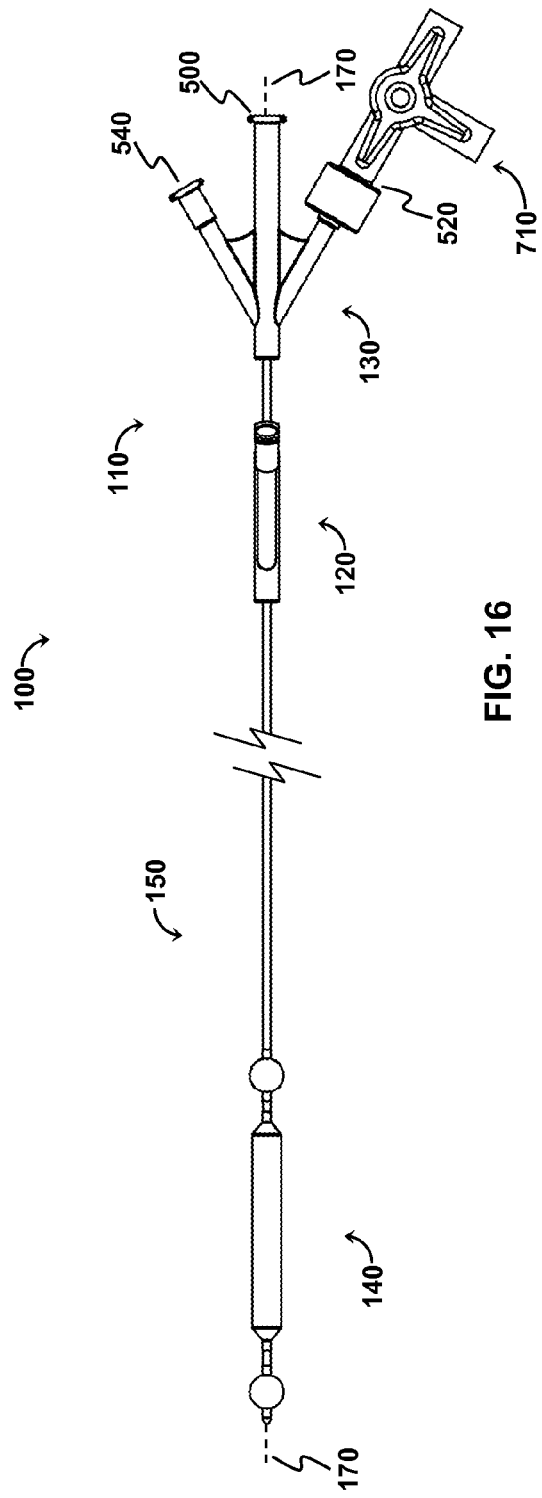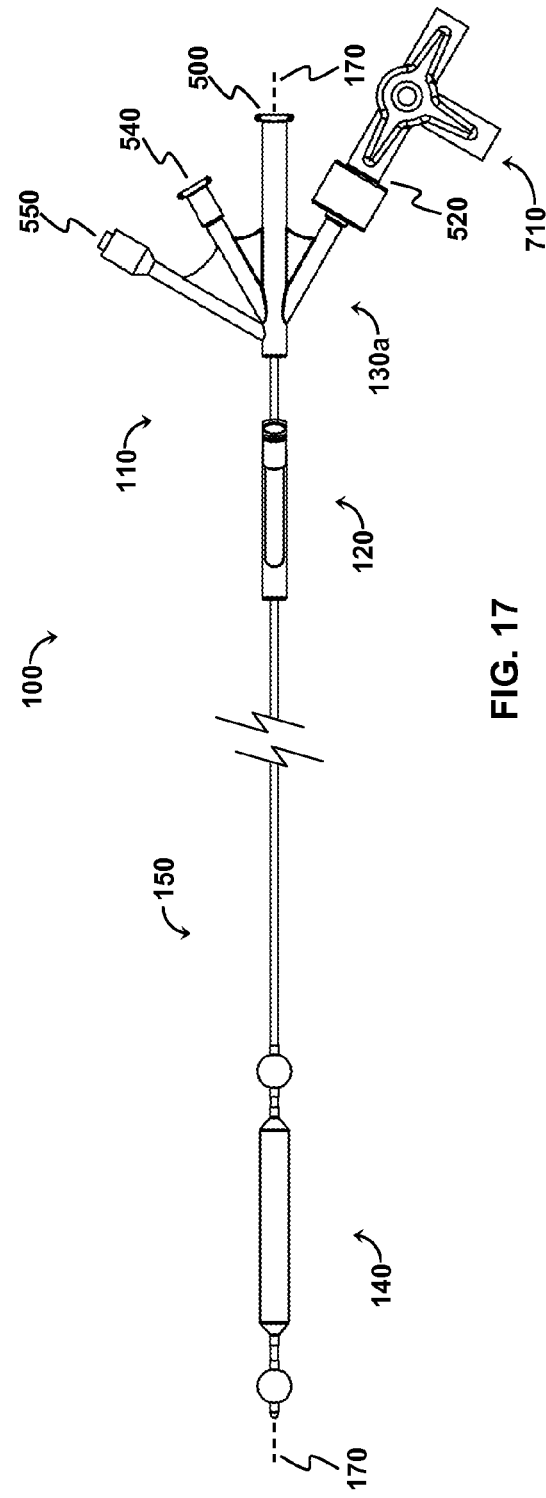
FIG. 16
FIG. 17

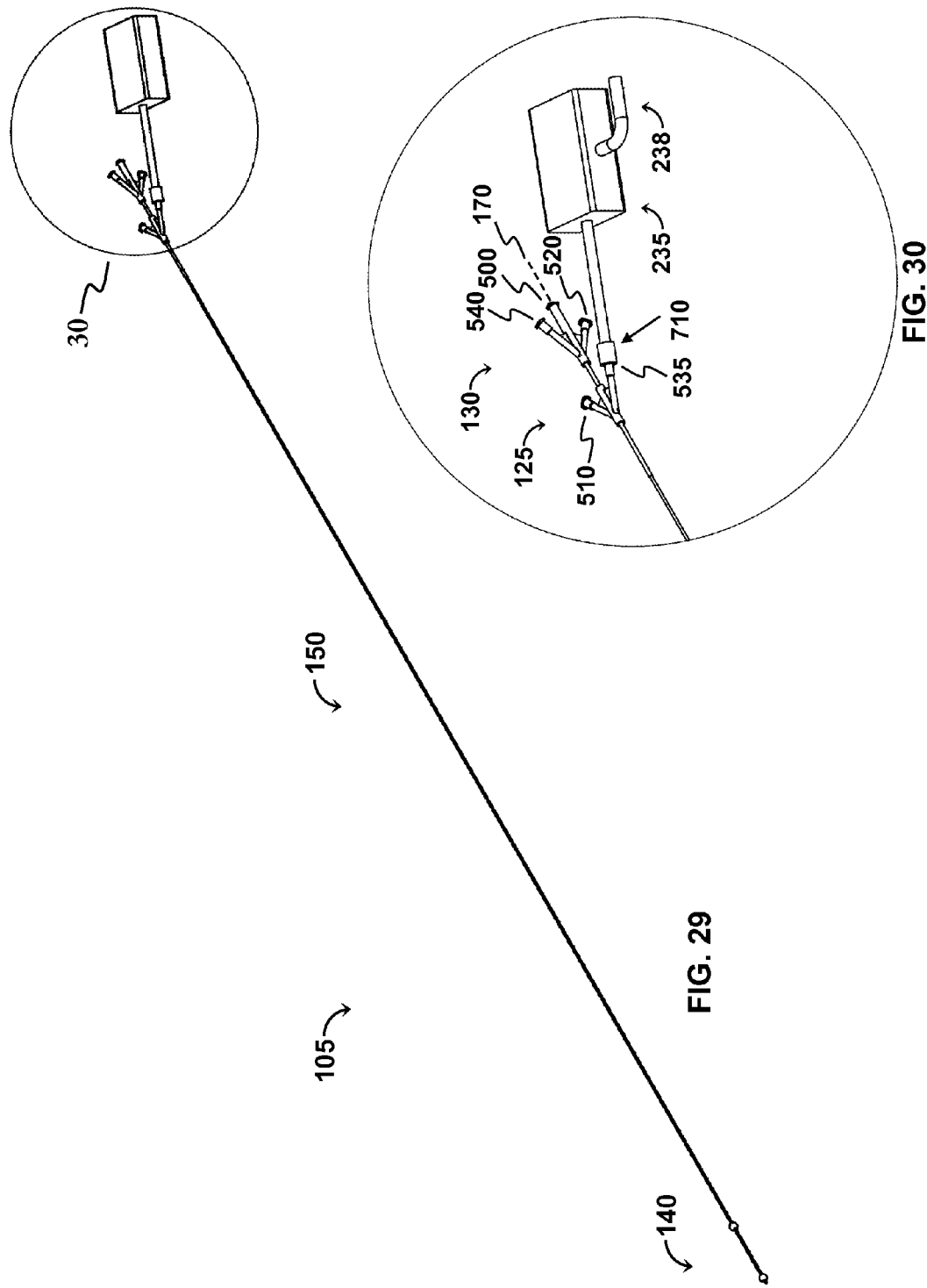

OCCLUSION PERFUSION CATHETER

CROSS-REFERENCE TO RELATED APPLICATIONS

This Non-Provisional Patent Application, filed under 35 U.S.C, §111(a), is a Continuation of co-pending application Ser. No. 12/611,796, filed on 3 Nov. 2009, which claims the benefit under 35 U.S.C. §119(e)(1) of U.S. Provisional Patent Application No. 61/110,744, filed under 35 U.S.C. §111(b) on 3 Nov. 2008, and which are hereby incorporated by reference in their entirety.

BACKGROUND

1. Field

The present disclosure relates generally to catheter devices and methods for the site-specific delivery of agents to biological spaces in medical procedures. More particularly, the present disclosure relates to catheter devices comprising multiple inflatable means carried by the catheters, with at least one radial opening located between at least a pair of inflatable means. The present disclosure also relates to methods for site-specific delivery of agents into blood vessels (including the blood vessel lumen and the vessel wall) for treatment of said blood vessels and/or other organ systems, as well as methods of visualizing the lumen of said blood vessels and/or other organ systems.

2. Description of Related Art

Regardless of the interventional treatment utilized to maintain vessel patency in vascular disease, there will always be restenosis and/or occlusions. The reason for this is that all of these treatment modalities create an intentional "controlled injury" of the vessel wall. In the healing process of this injury, neointimal hyperplasia (a form of scar tissue) develops. It develops because some of the cells of the vessel wall have been damaged, become "angry" (inflamed) and causes proliferation and migration of muscle cells from the media of the vessel wall into the lumen of the vessel. This process is called neointimal hyperplasia. The commonly-accepted method of controlling the development of neointimal hyperplasia is to treat it at the cellular level. These proliferating cells need the ability to function as normal cells and not become "angry". This can be accomplished by treating this "controlled injury" at the cellular level utilizing biopharmaceuticals, conventional small-molecule pharmaceuticals, live cells, or other new therapies (referred to collectively herein as "therapeutic agents" or simply "agents"). Pharmaceutical and other companies are gearing up to develop these live cells and therapies. This live cell technology has to be delivered locally to the area of "controlled injury" of the media of the vessel wall. Such therapies are particularly susceptible to environmental factors inherent to the delivery process, such as fluid pressure and shear stress, and devices of the prior art do not address these factors adequately.

Pharmaceutical companies have developed, or have the ability to develop, pharmaceuticals that will also affect proliferation and migration of these cells. The problem is that roost or all of these have the potential to be toxic when given systemically. However, when applied regionally to a localized area of "controlled injury" (e.g., in "controlled" or discrete amounts), these agents have the potential of being effective, but non-toxic (or at least significantly less toxic).

The technical problem underlying the present disclosure was therefore to overcome these prior art difficulties by creating devices providing for controlled, focal delivery and subsequent aspiration of therapeutic agents. The solution to this technical problem is provided by the embodiments characterized in the claims.

BRIEF SUMMARY

The present disclosure provides an improved agent delivery catheter that obviates the above-mentioned limitations, and further provides methods of using the same. The catheter provides a vehicle for local delivery of any of the aforementioned forms of therapy to a site of injury, as well as means for visualizing said site.

The catheter is a five-lumen catheter designed with at least two occlusion balloons, one proximal and one distal.

In one embodiment, a space-occupying balloon is provided between the two occlusion balloons, to occupy space, so producing an occlusion-perfusion catheter, or "OPC." When the space-occupying balloon is present and inflated, the result is a volume of space between the space occupying balloon, the two occlusion balloons, and the vessel wall—the area of controlled injury (the "treatment region"). In other words, the volume of said space is less than when the space-occupying balloon is either absent or is deflated. Pharmaceuticals, live cells, etc. ("agents") an then be injected into said space surrounding the balloons and bounded by the vessel wall. The agents can be perfused through the area(s) of controlled injury and optionally further forced into the media of the vessel wall via elevated fluid pressure (elevated pressure within the treatment region). The agent can then be aspirated as well, which may be important if toxic agents are used. The agent can be aspirated via the same catheter lumen used to inject the agent and/or via a separate dedicated catheter lumen. The intended result is to minimize restenosis of the vessel. Because an agent can be introduced into the treatment region via one catheter lumen and aspirated via a different catheter lumen, one may "flush" the treatment region if such is desired (e.g., with saline).

In one embodiment, a fiber optic device or other means known to those of ordinary skill in the art may be incorporated into the catheter to permit illumination and remote visualization of the treatment region ("visualization means"), so producing an occlusion-visualization catheter, or "OVC." In this embodiment, comprising visualization means, the space-occupying balloon is absent. Pharmaceuticals, live cells, etc. ("agents") can then be injected—via a dedicated catheter lumen—into the treatment region. The agents can be perfused through the area(s) of controlled injury and optionally further forced into the media of the vessel wall via elevated fluid pressure. The agent can then be aspirated as well, which may be important if toxic agents are used. The agent can be aspirated via the same catheter lumen used to inject the agent and/or via a separate dedicated catheter lumen. The intended result is to minimize restenosis of the vessel. Because an agent can be introduced into the treatment region via one catheter lumen and aspirated via a different catheter lumen, one may "flush" the treatment region if such is desired (e.g., with saline). By flushing the treatment region, one may improve visualization of the treatment region.

The device comprises a five-lumen extrusion, two occlusion balloons, a guide wire lumen, a perfusion lumen, an evacuation lumen, a balloon inflation huh, a therapeutic agent perfusion/evacuation/guide wire hub that allow selective access to the various lumens, and either visualization means, or a space occupying balloon. The purposes and functions of the five lumens are as follows: (a) guide wire lumen—allows the catheter to track over guide wire to treatment site; (b) space occupying balloon inflation lumen—allows inflation/ deflation control of space occupying balloon, or provides passage for visualization means; (c) therapeutic agent perfusion lumen—allows access to treatment region for perfusion of therapeutic agent; (d) occlusion balloon inflation lumen—allows simultaneous inflation/deflation control of occlusion balloons; and (e) evacuation lumen—allows evacuation of, or exit path from treatment region for therapeutic agent, or a second, individually controlled perfusion lumen for two-part therapeutic agents.

The two occlusion balloons, one distal and one proximal, define the treatment region (the area of controlled injury) as the volume contained between them. When present, the optional space occupying balloon allows adjustment of the treatment region volume (the volume between the two occlusion balloons) by simply adjusting the fill volume of the space occupying balloon. In other words, by inflating the space occupying balloon, less therapeutic agent is required to be delivered to the treatment region between the two occlusion balloons than would be required if the space occupying balloon were not inflated (or were absent entirely, as when the visualization means is provided).

In all cases, the OPC or OVC is delivered to the treatment site via a minimally invasive insertion technique (for example, the Seldinger technique). The applicants anticipate an "over the wire" or "rapid exchange" (i.e. "monorail") type of delivery, which are the two typical methods in use by interventional radiologists, cardiologists, and vascular surgeons, not to mention other medical specialists. It will be understood by those of ordinary skill in the art that other methods of delivery may be employed that keep within the spirit of the disclosure of the device and the method.

The present disclosure provides, in one embodiment, a five-lumen catheter comprising: a catheter shaft comprising a distal end and a proximal end, the distal end haying a shaft distal tip; a first balloon positioned on the shaft proximal to the shaft distal tip; a second balloon positioned on the shaft proximal to the first balloon; an agent delivery segment positioned on the shaft between the first and second balloons, distal to the second balloon, and having one orifice (the agent delivery segment skive) formed therein; an aspiration segment positioned on the shaft between the first and second balloons, proximal to the first balloon, and having one orifice (the aspiration segment skive) formed therein; visualization means positioned between the first and second balloons; a balloon inflation hub coupled to the shaft proximal end; a therapeutic agent perfusion/evacuation/guide wire hub coupled to the balloon inflation hub; and a guidewire lumen formed within the shaft and in communication with an opening formed in the distal end of the catheter and with an opening formed in the proximal end of the catheter. As will be appreciated by those of ordinary skill in the art, the aspiration segment may be positioned on the shaft between the first and second balloons and proximal to the agent delivery segment, or between the first and second balloons and distal to the agent delivery segment.

The present disclosure provides, in one embodiment, a five-lumen catheter comprising a catheter shaft comprising a distal end and a proximal end, the distal end having a shaft distal tip; a first balloon positioned on the shaft proximal to the shaft distal tip; a second balloon positioned on the shaft proximal to the first balloon; a third balloon positioned on the shaft proximal to the second balloon; an agent delivery segment positioned on the shaft between the second and third balloons and having one orifice formed therein; an aspiration segment positioned on the shaft between the first and second balloons and having one orifice formed therein; a balloon inflation hub coupled to the shaft proximal end; a therapeutic agent perfusion/evacuation/guide wire hub coupled to the balloon inflation hub; and a guidewire lumen formed within the shaft and in communication with an opening formed in the distil end of the catheter and with an opening formed in the proximal end of the catheter. As will be appreciated by those of ordinary skill in the art, the aspiration segment may be positioned on the shaft between the first and second balloons with the agent delivery segment positioned between the second and third balloons, or the aspiration segment may be positioned between the second and third balloons with the agent delivery segment positioned between the first and second balloons. Either of these arrangements are within the scope of the present disclosure.

In further embodiments, the catheters of the present disclosure optionally comprise a first pressure sensing means, whereby the pressure of the fluid environment at or near the agent delivery segment can be measured, known, or estimated. In this context, the term "fluid" indicates a continuous amorphous substance whose molecules and any suspended or dispersed components (e.g., cells, amino acids, polypeptides, nucleic acids, polynucleotides, vehicles, liposomes, nanoparticles, and combinations thereof) move freely past one another, has the tendency to assume the shape of its container (e.g., a liquid), and that is capable of flowing. It includes therapeutic agents injected via the device of the present disclosure, including but not limited to: solutions, drugs or other therapeutic agents dissolved in solution; cells suspended in solution; proteins dissolved or suspended in solution; nucleic acids dissolved or suspended in solution; vehicles (e.g., liposomes, micelles, vectors, nanoparticles, phospholipid dispersions, lamellar layers, liquid crystals, etc.); and combinations thereof. In this embodiment, the therapeutic agent perfusion/evacuation/guide wire hub further comprises a pressure sensor connector. The first pressure sensing means is contained at least partly within the agent perfusion lumen, and comprises a proximal and a distal end, where the distal end is located at or near the agent delivery segment skive and the proximal end is coupled to the pressure sensor connector.

In further embodiments, the OPC and OVC catheters of the present disclosure optionally comprise a second pressure sensing means (either independently of or together with the first pressure sensing means described above), having a proximal and a distal end, whereby the pressure of the fluid environment within the therapeutic agent perfusion lumen—at or near the perfusion skive—can be known or estimated. In this aspect, the second pressure sensing means may be located alongside the proximal end of the first pressure sensing means, with the second pressure sensing means proximal end also located at the pressure sensor connector, hut with the second pressure sensing means distal end located within the therapeutic agent perfusion lumen at or near the perfusion skive. Without intending to be bound to a particular pressure sensor, an example of a pressure sensor suitable for this embodiment is the FOP-MIV (Sequoia Technology, Ltd.; Reading, UK)—a fiber optic pressure sensor.

In further embodiments, the catheters of the present disclosure optionally comprise a first two- or three-way valve or check valve in fluid communication with the perfusion port and the therapeutic agent delivery lumen so that fluid may be delivered—but not aspirated—via the agent delivery segment. In related embodiments, the catheters of the present disclosure optionally comprise a second two- or three-way valve or check valve in fluid communication with the aspiration port and the aspiration lumen no that fluid may be aspirated—but not delivered—via the aspiration segment. In preferred embodiments, the catheters of the present disclosure optionally comprise a first two- or three-way valve or check valve in fluid communication with the perfusion port and the therapeutic agent delivery lumen, and a second two- or three-way valve or check valve in fluid communication with the aspiration port and the aspiration lumen. The optional first and/or second two- or three-way valve or check valves may be present either independently of or together with the first pressure sensing means described above and/or the second pressure sensing means described above.

Disclosed herein is a catheter comprising: a catheter shaft having a distal end having a shaft distal tip and a proximal end; a first balloon positioned on the shaft proximal to the shaft distal tip; a second balloon positioned on the shaft proximal to the first balloon; a third balloon positioned on the shaft proximal to the second balloon; an agent delivery segment positioned on the shaft between the first and third balloons and having one orifice formed therein; an aspiration segment positioned on the shaft between the first and third balloons and having one orifice formed therein; and a guidewire lumen formed within the shaft and in communication with: an opening formed in a proximal end of the catheter; and an opening formed in a distal end of the catheter.

In one embodiment, the catheter may further comprise a first pressure-sensing means having proximal and distal ends and a length therebetween, wherein said distal end is at or near the agent delivery segment orifice. Furthermore, said first pressure-sensing means proximal end is in communication with a connector formed on the proximal end of the catheter shaft.

In one embodiment, the catheter may further comprise a first inflation lumen in communication with the first and third balloons. The first inflation lumen may be further in communication with a first balloon inflation port formed on the proximal end of the catheter shaft.

In one embodiment, the catheter may further comprise a second inflation lumen in communication with the second balloon. Furthermore, the second inflation lumen may be further in communication with a second balloon inflation port formed on the proximal end of the catheter shaft.

In one embodiment, the catheter may further comprise an aspiration lumen in communication with the aspiration segment orifice. Furthermore, the aspiration lumen may be further in communication with an aspiration port formed on the proximal end of the catheter shaft.

In one embodiment, the catheter may further comprise a valve in communication with said aspiration port.

In one embodiment, the catheter may further comprise an agent delivery lumen in communication with the agent delivery segment orifice. Furthermore, the agent delivery lumen may be further in communication with an agent delivery port formed on the proximal end of the catheter shaft.

In one embodiment, the catheter may further comprise a first pressure-sensing means having proximal and distal ends and a length therebetween, wherein said first pressure-sensing means proximal end is in communication with a connector formed on the proximal end of the catheter shaft and said first pressure-sensing means distal end is at or near the agent delivery segment orifice.

In one embodiment, the catheter may further comprise a second pressure-sensing means having proximal and distal ends and a length therebetween, wherein said second pressure-sensing means proximal end is in communication with the connector formed on the proximal end of the catheter shaft and said second pressure-sensing means distal end is located within the agent delivery lumen.

Also disclosed herein is a catheter comprising: a catheter shaft having a distal end having a shaft distal tip and a proximal end; a first balloon positioned on the shaft proximal to the shaft distal tip, a second balloon positioned on the shaft proximal to the first balloon, and a third balloon positioned on the shaft proximal to the second balloon; a first inflation lumen in communication with the first and third balloons, wherein said first inflation lumen is further in communication with a first balloon inflation port formed on the proximal end of the catheter shaft; a second inflation lumen in communication with the second balloon, wherein said second inflation lumen is further in communication with a second balloon inflation port formed on the proximal end of the catheter shaft; an agent delivery segment positioned on the shaft between the second and third balloons and having one orifice formed therein, wherein the agent delivery lumen is in communication with the agent delivery segment orifice and an agent delivery port formed on the proximal end of the catheter shaft; an aspiration segment positioned on the shaft between the first and second balloons and having one orifice formed therein, wherein the aspiration lumen is in communication with the aspiration segment orifice and an aspiration port formed on the proximal end of the catheter shaft, said aspiration port optionally further comprising a valve in communication with the aspiration port; a guidewire lumen formed within the shaft and in communication with an opening formed in a proximal end of the catheter and an opening formed in a distal end of the catheter; a first pressure-sensing means having proximal and distal ends and a length therebetween, wherein said first pressure-sensing means proximal end is in communication with a connector formed on the proximal end of the catheter shaft and said first pressure-sensing means distal end is at or near the agent delivery segment orifice; and a second pressure-sensing means having proximal and distal ends and a length therebetween, wherein said second pressure-sensing means proximal end is in communication with the connector formed on the proximal end of the catheter shaft and said second pressure-sensing means distal end is located within the agent delivery lumen.

Also described herein is a catheter comprising: a catheter shaft having a distal end having a shaft distal tip and a proximal end; first balloon positioned on the shaft proximal to the shaft distal tip; a second balloon positioned on the shaft proximal to the first balloon; an agent delivery segment positioned on the shaft between the first and second balloons and having one orifice formed therein; an aspiration segment positioned on the shaft between the first and second balloons and having one orifice formed therein; a visualization means, wherein said visualization means enables visualization between the first and second balloons; and a guidewire lumen formed within the shaft and in communication with an opening formed in a proximal end of the catheter; and an opening formed in a distal end of the catheter. In one embodiment, the catheter may further comprise a first inflation lumen in communication with the first and second balloons, wherein said first inflation lumen is further in communication with a first balloon inflation port formed on the proximal end of the catheter shaft. In one embodiment, the catheter may further comprise a visualization means lumen in communication with a visualization means slot and containing at least a portion of said visualization means. In one embodiment, the catheter may further comprise an aspiration lumen in communication with the aspiration segment orifice, wherein said aspiration lumen is further in communication with an aspiration port formed on the proximal end of the catheter shaft. In one embodiment, the catheter may further comprise an agent delivery lumen in communication with the agent delivery segment orifice wherein said agent delivery lumen is further in communication with an agent delivery port formed on the proximal end of the catheter shaft.

BRIEF DESCRIPTION OF THE DRAWINGS

For a further understanding of the nature, objects, and advantages of the devices and methods of the present disclosure, reference should be had to the following detailed description, read in conjunction with the following drawings, wherein like reference numerals denote like elements.

FIG. 3 is a cross-sectional view taken along line B-B as shown in FIG. 1, displaying a distal occluding balloon, five lumens which may be employed to inflate and deflate balloons or deliver and remove therapeutic agents or biologic samples, and a skive port extending through the thickness of the catheter wall such that occluding balloon inflation lumen of the catheter is in communication with the catheter exterior wall for inflating and deflating the distal occluding balloon.

FIG. 4 is a cross-sectional view taken along line C-C as shown in FIG. 1, displaying five lumens which may be employed to inflate and deflate balloons or to deliver and remove therapeutic agents, and an aspiration skive port extending through the thickness of the catheter wall such that aspiration lumen of the catheter is in communication with the catheter exterior wall for aspirating therapeutic agents or fluid samples from the lumen of a blood vessel.

FIG. 5 is a cross-sectional view taken along line D-D as shown in FIG. 1, displaying a space occupying balloon, five lumens which may be employed to inflate and deflate balloons or to deliver and remove therapeutic agents, and a skive port extending through the thickness of the catheter wall such that space-occupying balloon inflation lumen of the catheter is in communication with the catheter exterior wall for inflating and deflating the space occupying balloon.

FIG. 6 is a cross-sectional view taken along line E-E as shown in FIG. 1, displaying five lumens which may be employed to inflate and deflate balloons or to deliver and remove therapeutic agents, and a skive port extending through the thickness of the catheter wall such that therapeutic agent delivery lumen of the catheter is in communication with the catheter exterior wall for delivering therapeutic agents to the lumen of a blood vessel.

FIG. 7 is a cross-sectional view taken along line F-F as shown in FIG. 1, displaying a proximal occluding balloon, five lumens which may be employed to inflate and deflate balloons or to deliver and remove therapeutic agents, and a skive port extending through the thickness of the catheter wall such that occluding balloon inflation lumen of the catheter is in communication with the catheter exterior wall for inflating and deflating the proximal occluding balloon.

FIG. 8 is a side view of the catheter assembly of the present disclosure, showing the therapeutic agent perfusion/aspiration and guidewire hub (the "perfusion/aspiration hub") in a plane perpendicular to the balloon inflation hub.

FIG. 9 is a cross-sectional side view of the balloon inflation hub of the present disclosure, taken along the line H-H, as shown in FIG. 8. For the sake of clarity, the therapeutic agent perfusion/aspiration and guidewire hub is not shown in this FIG. 9.

FIG. 10 is a side view of the catheter assembly of the present disclosure, showing the balloon inflation hub in a plane perpendicular to the therapeutic agent perfusion/aspiration and guidewire hub.

FIG. 11 is a cross-sectional side view of therapeutic agent perfusion/aspiration and guidewire hub of the present disclosure, taken along the line G-G, as shown in FIG. 10. For the sake of clarity, the balloon inflation hub is not shown in this FIG. 11.

FIGS. 12A and 12B show an embodiment of an aspect of a catheter of the present disclosure which has been inserted into a blood vessel. For clarity, the entire device has not been shown and the figure is not drawn to scale. FIG. 12A shows the distal portion of the catheter of the present disclosure with the distal and proximal occluding balloons inflated, and the space occupying balloon deflated. FIG. 12B shows the result of inflating space occupying balloon.

FIG. 16 is a plan view of the catheter assembly of the present disclosure, showing three-way stopcock in line with aspiration port of therapeutic agent perfusion/aspiration/guidewire hub.

FIG. 17 is a plan view of the catheter assembly of the present disclosure, showing three-way stopcock in line with aspiration port of therapeutic agent perfusion/aspiration/guidewire/pressure sensor hub.

FIG. 29 is a perspective view of a catheter of the present invention, showing the visualization means attachment to the proximal end adapter.

FIG. 30 depicts detail 30, as indicated in FIG. 29, and shows the visualization means attachment to the proximal end adapter

DETAILED DESCRIPTION

Figure 1:
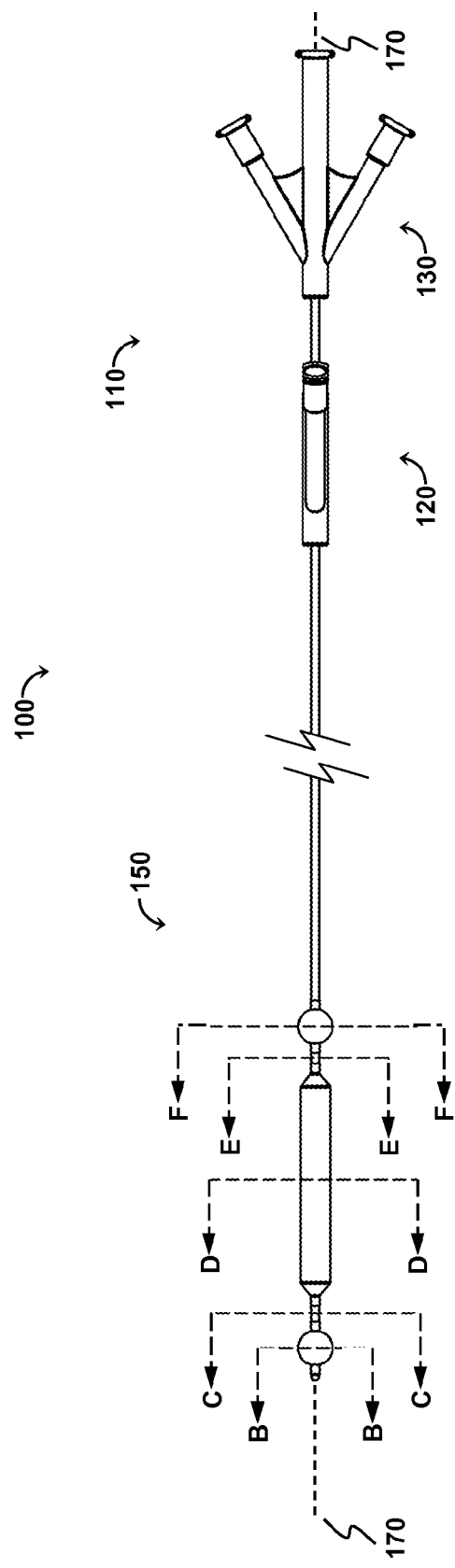
FIG. 1 shows a side elevational view of one embodiment of a catheter of the present disclosure. For clarity, the entire device has not been shown and the figure is not drawn to scale. The jagged line M-M represents a break in the continuum of the catheter.

Before the catheter of the present disclosure is further described, it is to be understood that the disclosure is not limited to the particular embodiments described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

As used herein, the term "skive" or "skive port" is synonymous with "orifice."

As illustrated in FIGS. 1, 2, 12A and 12B, one embodiment of the catheter assembly (100) comprises a catheter (150) extending from a proximal end adapter (110) and longitudinally movable within a vessel (10) (see FIGS. 12A and 12B) along the catheter longitudinal axis (170). Catheter (150) includes elongate catheter shaft (160) having longitudinal axis (170) and defining five lumens therein. At its distal end (140), the catheter assembly (100) has an atraumatic tapered distal tip (200). A distal occluding balloon (210) is located proximal to the tapered distal tip (200) along the longitudinal axis (170) of the catheter (150), a space-occupying balloon (230) is located proximal to the distal occluding balloon (210) along the longitudinal axis (170) of the catheter (150), and a proximal occluding balloon (250) is located proximal to the space-occupying balloon (230) along the longitudinal axis (170) of the catheter (150). Between the distal occluding balloon (210) and the space-occupying balloon (230) is an aspiration segment (220), and between the space-occupying balloon (230) and the proximal occluding balloon (250) is located an agent delivery segment (240). Each of the aspiration segment (220) and the agent delivery segment (240) have at least one skive port (420 and 440, respectively) formed therein (see also: FIGS. 12A and 12B). Proximal end adapter (110) includes occluding balloon inflation hub (120) and delivery hub (130).

Figure 2:
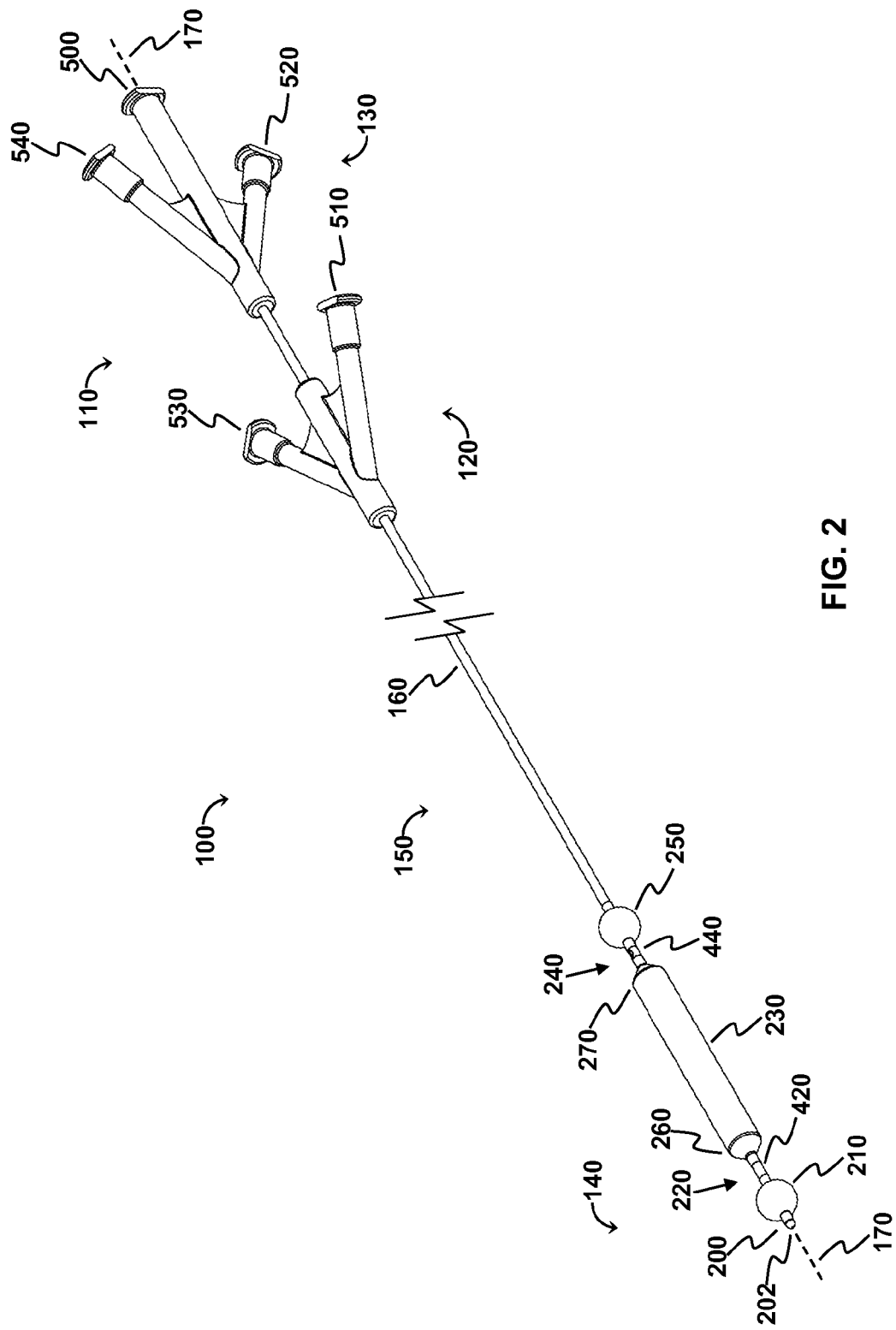
FIG. 2 is a perspective view of one embodiment of a catheter of the present disclosure in its assembled form.
Figure 13:
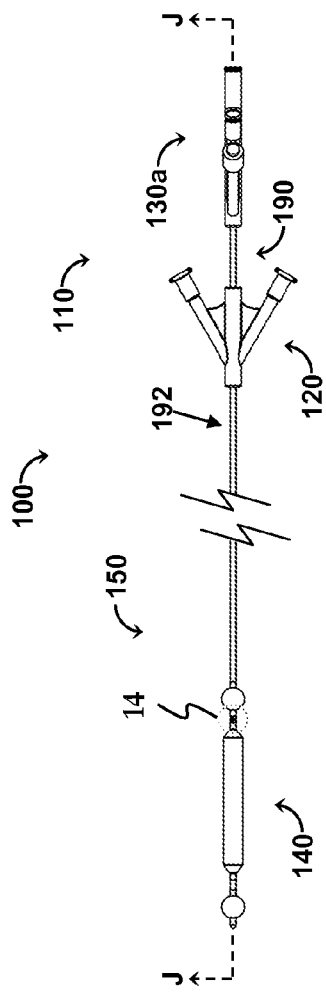
FIG. 13 is a plan view of a catheter assembly of the present disclosure, showing the therapeutic agent perfusion/aspiration/guidewire/pressure sensor hub in a plane perpendicular to the balloon inflation hub.

As seen in FIGS. 1, 2, and 9, occluding balloon inflation hub (120) comprises distal and proximal occluding balloon inflation port (510) and space-occupying balloon inflation port (530). Distal and proximal occluding balloon inflation port (510) communicates with distal and proximal occluding balloon inflation lumen (310) via skive port (610), and permits distal and proximal occluding balloons (210 and 250, respectively), discussed below, to be inflated and deflated—in tandem—during use. Space-occupying balloon inflation port (530) communicates with space occupying balloon inflation lumen (330) via skive port (630), and permits space-occupying balloon (230), discussed below, to be inflated and deflated—independently of the distal and proximal occluding balloons—during use.

As seen in FIGS. 1, 2, and 11, therapeutic agent perfusion/aspiration and guidewire hub (the "perfusion/aspiration hub," 130) comprises therapeutic agent delivery port (540), therapeutic agent aspiration port (520), and guidewire port (500). Therapeutic agent delivery port (540) communicates with therapeutic agent delivery lumen (340) via skive port (640), and permits delivery of therapeutic agent via skive port (440) to the lumen (18) of a blood vessel (10). Therapeutic agent aspiration port (520) communicates with aspiration lumen (320) via skive port (620), and permits aspiration of therapeutic agents or fluid samples via skive port (420) from the lumen (18) of a blood vessel (10) (see, e.g., FIG. 12B). Guidewire port (500) is in communication with guidewire lumen (300), which extends the entire length of the catheter (150) to emerge at atraumatic tapered tip (200) as distal opening (202), and permits "over-the-wire" use. As will be appreciated by those of ordinary skill in the art, and as indicated by the jagged line breaks in FIGS. 1, 2, 8, 10, 12A, 12B, 13, and 15-18, the catheter (100) may be either longer or shorter so that the distal end (140) may reach the desired location within a patient while the proximal end adapter (110) remains outside the patient. Between therapeutic agent perfusion/aspiration and guidewire hub (130) and occluding balloon inflation hub (120), the catheter (180) possesses three lumens (300, 320, 340).

Referring now to FIGS. 1-3, 9, and 11, FIG. 3 is a cross-sectional view of the catheter of FIG. 1 taken along line B-B, and illustrates: distal occluding balloon (210); guidewire lumen (300), which communicates with guidewire port (500); distal and proximal occluding balloon inflation lumen (310), which communicates with occlusion balloon inflation port (510) via skive port (610); space occupying balloon inflation lumen (330), which communicates with space-occupying balloon inflation port (530) via skive port (630); aspiration lumen (320), which communicates with aspiration port (520) via skive port (620); therapeutic agent delivery lumen (340), which communicates with drug delivery port (540) via skive port (640); and distal occluding balloon inflation skive port (410). Distal occluding balloon inflation skive port (410) extends through the thickness of the catheter exterior wall (380) such that occluding balloon inflation lumen (310) of the catheter (150) is in communication with the catheter exterior wall (380) for inflating the distal occluding balloon (210).

Referring now to FIGS. 1, 2, 4, 9, and 11, FIG. 4 is a cross-sectional view of the catheter of FIG. 1 taken along line C-C, and illustrates a cross-sectional view of the therapeutic agent aspiration segment (220). Referring now to FIGS. 1, 2, 4, 9, and 11, FIG. 4 shows: guidewire lumen (300), which communicates with guidewire port (500); distal and proximal occluding balloon inflation lumen (310), which communicates with occlusion balloon inflation port (510) via skive port (610); space occupying balloon inflation lumen (330), which communicates with space-occupying balloon inflation port (530) via skive port (630); aspiration lumen (320), which communicates with aspiration port (520) via skive port (620); therapeutic agent delivery lumen (340), which communicates with perfusion port (540) via skive port (640); and aspiration skive port (420). Aspiration skive port (420) extends through the thickness of the catheter exterior wall (380) such that aspiration lumen (320) of the catheter (150) is in communication with the catheter exterior wall (380) for aspirating therapeutic agents or liquid samples from the lumen (18) of a blood vessel (10) (see, e.g., FIGS. 12A and 12B).

Referring now to FIGS. 1, 2, 5, 9, and 11, FIG. 5 is a cross-sectional view of the catheter of FIG. 1 taken along line D-D, and illustrates: space-occupying balloon (230); guidewire lumen (300), which communicates with guidewire port (500); distal and proximal occluding balloon inflation lumen (310), which communicates with occlusion balloon inflation port (510) via skive port (610); space occupying balloon inflation lumen (330), which communicates with space-occupying balloon inflation port (530) via skive port (630); aspiration lumen (320), which communicates with aspiration port (520) via skive port (620); therapeutic agent delivery lumen (340), which communicates with drug delivery port (540) via skive port (640); and space-occupying balloon inflation skive port (430). Space-occupying balloon inflation skive port (430) extends through the thickness of the catheter exterior wall (380) such that space-occupying balloon inflation lumen (330) of the catheter (150) is in communication with the catheter exterior wall (380) for inflating and deflating the space occupying balloon (230).

FIG. 6 is a cross-sectional view of the catheter of FIG. 1 taken along line E-E, and illustrates a cross-sectional view of the therapeutic agent delivery segment (240). Referring now to FIGS. 1, 2, 6, 9, and 11, FIG. 6 shows: guidewire lumen (300), which communicates with guidewire port (500); distal and proximal occluding balloon inflation lumen (310), which communicates with occlusion balloon inflation port (510) via skive port (610); space occupying balloon inflation lumen (330), which communicates with space-occupying balloon inflation port (530) via skive port (630); aspiration lumen (320), which communicates with aspiration port (520) via skive port (620); therapeutic agent delivery lumen (340), which communicates with perfusion port (540) via skive port (640); and drug delivery skive port (440). Drug delivery skive port (440) extends through the thickness of the catheter exterior wall (380) such that drug delivery lumen (340) of the catheter (150) is in communication with the catheter exterior wall (380) for delivering therapeutic agents to the lumen (18) of a blood vessel (10) (see, e.g., FIGS. 12A and 12B).

Referring now to FIGS. 1, 2, 7, 9, and 11, FIG. 7 is a cross-sectional view of the catheter of FIG. 1 taken along line F-F. FIG. 7 illustrates: proximal occluding balloon (250); guidewire lumen (300), which communicates with guidewire port (500); distal and proximal occluding balloon inflation lumen (310), which communicates with occlusion balloon inflation port (510) via skive port (610); space occupying balloon inflation lumen (330), which communicates with space-occupying balloon inflation port (530) via skive port (630); aspiration lumen (320), which communicates with aspiration port (520) via skive port (620); therapeutic agent delivery lumen (340), which communicates with drug delivery port (540) via skive port (640); and proximal occluding balloon inflation skive port (450). Proximal occluding balloon inflation skive port (450) extends through the thickness of the catheter exterior wall (380) such that occluding balloon inflation lumen (310) of the catheter (150) is in communication with the catheter exterior wall (380) for inflating the proximal occluding balloon (250).

Referring to FIGS. 3-7, the catheter (160) has a catheter exterior wall (380) and a catheter interior wall (390). As may be appreciated from FIGS. 2, 3-7, 9, and 11, the catheter interior wall (390) defines the guide wire lumen (300). Lumens (330, 340, 310, 320) are peripheral to guidewire lumen (300); they are formed within the catheter (150) and located between the catheter interior wall (390) and the catheter exterior wall (380). The five lumens (300, 310, 340, 330, 320) extend longitudinally through the catheter (150), interconnecting the open proximal end (500, 510, 540, 530, and 520, respectively) with the open distal end (202, 410/450, 440, 430, and 420, respectively).

As seen in FIGS. 8 and 9, balloon inflation hub (120) is a component of the proximal end adapter (110), lying proximal to the distal end (140) and distal to the therapeutic agent perfusion/aspiration and guidewire hub (130). It will be appreciated by those of ordinary skill in the art that the positions of the balloon inflation hub (120) and the therapeutic agent perfusion/aspiration and guidewire hub (130) may be reversed with respect to one another so that the therapeutic agent perfusion/aspiration and guidewire hub (130) lies between the distal end (140) and the balloon inflation hub (120).

The balloon inflation hub (120) is comprised of occlusion balloon inflation port (510), space occupying balloon inflation port (530), and catheter shaft (160). Occlusion balloon inflation port (510) is communicably connected to occlusion balloon inflation lumen (310) of catheter shaft (160) via occlusion balloons hub inflation skive (610). Space occupying balloon inflation port (530) is communicably connected to space occupying balloon inflation lumen (330) of catheter shaft (160) via space occupying balloon hub inflation skive (630).

As seen in FIGS. 10 and 11, therapeutic agent perfusion/aspiration and guidewire hub (130) is a component of the proximal end adapter (110), lying proximal to the distal end (140) and proximal to the balloon inflation hub (120). The therapeutic agent perfusion/aspiration and guidewire hub (130) is comprised of therapeutic agent perfusion port (540), aspiration port (520), guidewire port (500), and catheter shaft (160). Therapeutic agent perfusion port (540) is communicably connected to therapeutic agent perfusion lumen (340) of catheter shaft (160) via perfusion hub skive (640). Aspiration port (520) is communicably connected to aspiration lumen (320) of catheter shaft (160) via aspiration hub skive (620). Guidewire port (500) is communicably connected to guidewire lumen (300), which encloses the longitudinal axis (170) of the OPC (100). In the present embodiment, and as shown in FIGS. 3-7, the longitudinal axis (170) is centered within the circular cross-section of the guidewire lumen (300).

FIGS. 12A and 12B show the distal and proximal occlusion balloons (210, 250) as they would appear when inflated inside a vessel (10) or other hollow body structure. It will be appreciated by those of ordinary skill in the art that occluding balloons (210, 250), space-occupying balloon (230), catheter (150, 160), and other components of the device of the present disclosure (100) may be sized appropriately to account for the dimensions that would be required in other hollow body structures (for example, but without intending to be limited, vessels of the lymphatic system, the gastroesophageal tract, the portal-caval system of the liver, the gall bladder and bile ducts, the urinary system, the respiratory system, ducts of the endocrine and exocrine organs, and reproductive organs). FIGS. 12A and 12B show space-occupying balloon (230) as it would appear before inflation and after inflation, respectively. Referring to FIGS. 2, 12A, and 12B, distal and proximal radio-opaque marker bands (260, 270, respectively) are also shown located on the "shoulders" of the space-occupying balloon (230) to facilitate visualization, under fluoroscopic imaging, of the catheter (150) within a vessel (10). It will be appreciated by those of ordinary skill in the art that radio-opaque markers may also be located upon the catheter shaft (for example, and without limitation, along the aspiration segment (220) or the therapeutic agent delivery segment (240). More preferably, one of the marker bands is located on the shaft (150) at the most distal portion of the aspiration segment (220), and a second marker band is located on the shaft (150) at the most proximal portion of the therapeutic agent delivery segment (240). Alternatively, one of the marker bands is located on the shaft (150) at or near distal occlusion balloon inflation skive (FIG. 3, 410), and a second marker band is located on the shaft (150) at or near proximal occluding balloon inflation skive (FIG. 7, 450). In either of these embodiments, the gap between the two radio-opaque marker bands aids in approximating the treatment volume and treatment location. It will also be appreciated that one marker band may be used, instead of a plurality. The marker bands (260, 270) may optionally be rotationally specific (e.g., having a generally "U-shaped" configuration) so that the rotational position of the distal end (140) of the catheter (150) will be apparent when the markers are observed in a two-dimensional fluoroscopic image. Alternatively, contrast fluid may be used to inflate any one or all of the balloons (210, 230, and/or 250), or may be injected through drug delivery skive port (440) or through guidewire lumen (300) to emerge at the distal tapered tip (200) from the opening (202).

As seen in FIG. 12A, the inflation of distal and proximal occlusion balloons (210, 250) inside the lumen (20) of a blood vessel (10), without inflation of space-occupying balloon (230), leads to their contact with vessel endothelium (50) and occlusion of a comparatively large intraluminal space (30). Subsequent inflation of the space occupying balloon (230), as shown in FIG. 12B, reduces the intraluminal volume exterior to the balloons to produce occlusion of a comparatively small intraluminal space (40), and thus reduces the treatment volume of the targeted vessel segment (60). By "treatment volume" is meant the volume of the vessel, between the expanded occlusion balloons (210, 250), minus the volume of the space-occupying balloon (230). Consequently, deflation of the space-occupying balloon leads to increased treatment volume while inflation of the space-occupying balloon reduces the treatment volume. As can be seen in FIG. 12B, fluid communication between therapeutic agent delivery segment (240) and aspiration segment (220) is maintained (40) despite inflation of space-occupying balloon (230) because the balloon (230) is not in contact with vessel endothelium (50).

As shown in FIGS. 3-7, the longitudinal axis (170) is contained within the guide wire lumen (300), but persons having ordinary skill in the art will recognize that the arrangement of lumens may be altered to offset the central lumen (300) from the longitudinal axis (170). Lumens (330, 340, 310, and 320) are formed within the catheter (150) and are located substantially between the catheter exterior wall (380) and the catheter interior wall (390). The lumens (300, 330, 340, 310, and 320) extend longitudinally through the catheter (150), but only guidewire lumen (300) is patent along the entire length of the catheter (150), emerging at the distal tapered tip (200) as opening (202) and so allowing "over-the-wire" use.

Inflation of the distal occluding balloon (210) and the proximal occluding balloon (250) creates a substantially cylindrical delivery region bounded distally and proximally by the inflated distal and proximal occluding balloons (210 and 250, respectively) and bounded circumferentially by vessel (10), as shown in FIG. 12A. Distal and proximal occluding balloons (210 and 250, respectively) are constructed of a compliant to semi-compliant material (e.g., without limitation, polyethylene terephthalate, nylon, polyurethane, or other thermoplastic polymers), which means that they retain their shape as they generate force and form a seal against blood flow without imparting excessive pressure to the blood vessel. With only the distal and proximal occluding balloons (210 and 250, respectively) inflated and the space-filling balloon (230) deflated, though, a relatively large treatment volume remains within the occluded vessel lumen (30), as shown in FIG. 12A. This large volume is particularly undesirable when scarce or expensive agents are delivered; it is potentially harmful when toxic agents are to be delivered because a greater volume of those agents is required. The greater treatment volume thus produces increased expense and risk.

Inflation of the space-occupying balloon (230) dramatically reduces the space remaining within the occluded vessel lumen (40), as shown in FIG. 12B, thereby increasing the effective application of agent delivered while simultaneously reducing the amount of agent needed. The space occupying balloon (230) is constructed of a non-compliant to semi-compliant material (e.g., without limitation, polyurethane, nylon elastomers, polyethylene terephthalate, or other thermoplastic polymers). The space-occupying balloon (230) is inflated to a degree that it does not contact the vessel endothelium (50), thus leaving the entire region of endothelium (50) between the inflated distal and proximal occluding balloons (210 and 250, respectively) available for exposure to the delivered agent.

In one embodiment, the guide wire lumen (300) provides access to a guidewire (not shown), via distal opening (202) in atraumatic tapered tip (200), while distal and proximal occluding balloon inflation lumen (310) and space-occupying balloon inflation lumen (330) provide access for balloon inflation ports (510 and 530, respectively) for the distal (210) and proximal (250) occluding balloons and for the space-occupying balloon (230), respectively. Agent delivery port (540) is in communication with agent delivery lumen (340) via skive port (640), and agent delivery lumen (340) is also in communication with vessel lumen (18) via skive port (440) at agent delivery segment (240), for the delivery of therapeutic agents to the occluded vessel lumen (18, 30, 40). Aspiration port (520) is in communication with aspiration lumen (320) via skive port (620), and aspiration lumen (320) is in communication with vessel lumen (18) via skive port (420) at aspiration segment (220), for aspiration of agents or other fluid samples from the vessel lumen (18, 30, 40). In one aspect of this embodiment, there may be provided a two- or three-way valve or check valve (710) in fluid communication with the agent delivery lumen (340), the aspiration lumen (320, as shown in FIGS. 16 and 17), or both, to prevent injection via the aspiration lumen (320), aspiration or backflow via the agent delivery lumen (340), or both (respectively).

Figure 14:
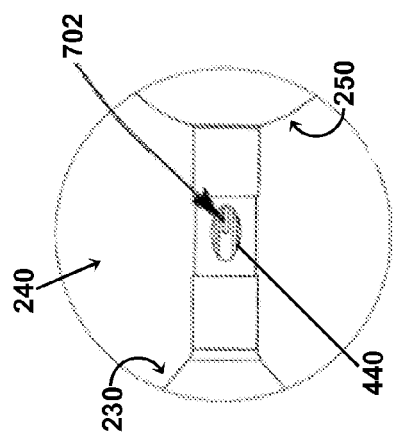
FIG. 14 depicts detail 14, as indicated in FIG. 13, and shows the distal end of the pressure sensing means, located at the therapeutic agent delivery segment.
Figure 15:
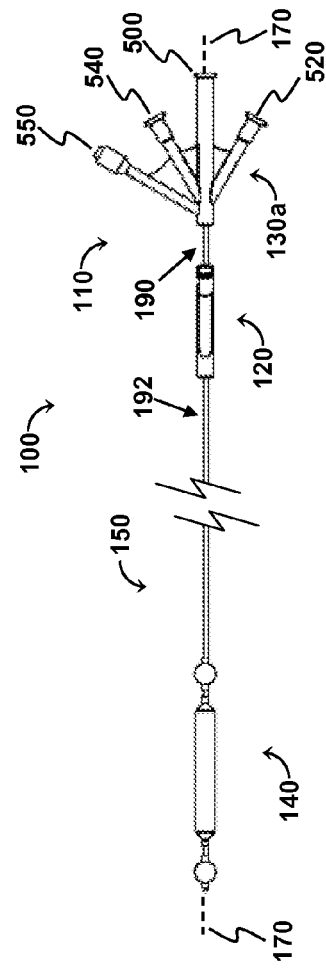
FIG. 15 is a plan view of the catheter assembly of the present disclosure, showing the therapeutic agent perfusion/aspiration/guidewire/pressure sensor hub in a plane perpendicular to the balloon inflation hub, and showing the pressure sensor connector.
Figure 18:
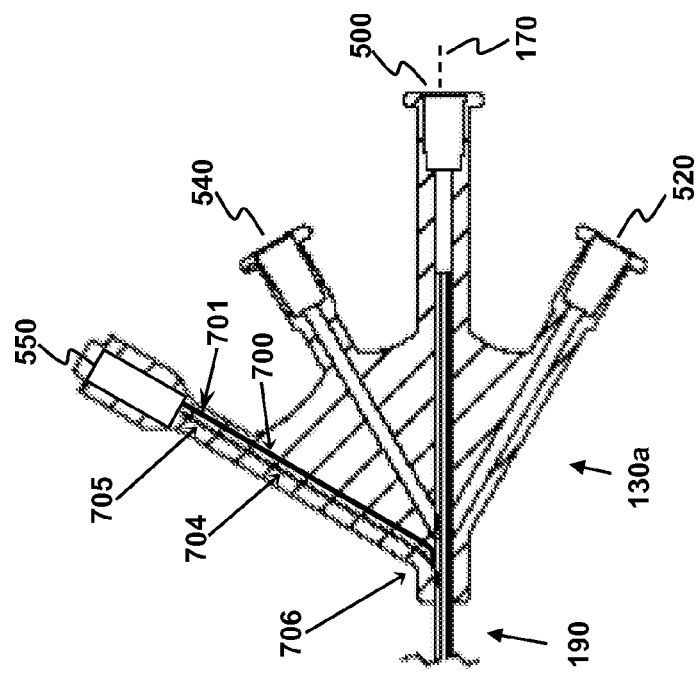
FIG. 18 is a cross-sectional side view of therapeutic agent perfusion/aspiration/guidewire/pressure sensor hub of the present disclosure, taken along the line J-J, as shown in FIG. 13. For the sake of clarity, the balloon inflation hub is not shown in this FIG. 18.
Figure 18:
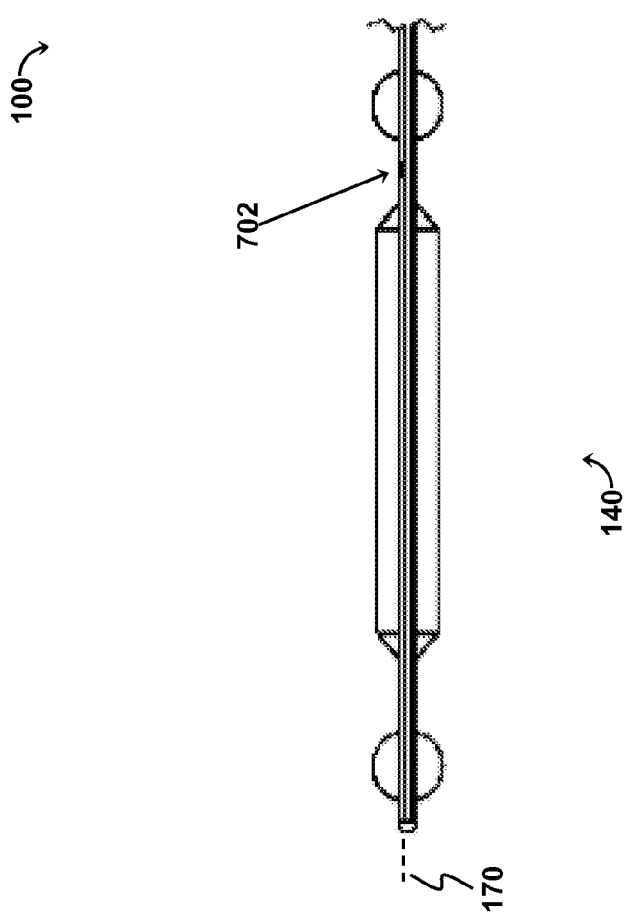

In another aspect of this embodiment, the catheter (100) may include a first pressure sensing means (700), as seen in FIGS. 13-15 and 18, incorporated into the catheter shaft (190, 192) and hub (130a) of the adapter (110). Without intending to be limited thereby, an example of a suitable pressure sensing means (700) is the FOP-MIV (Sequoia Technology, Ltd.; Reading, UK)—a fiber optic pressure sensor. Such pressure sensing means has a distal end (702), a proximal end (701) located at pressure sensor connector (550), and a length therebetween. Via pressure sensor connector (550), which is in fluid communication with therapeutic agent perfusion lumen (340), the pressure sensing means enters therapeutic agent perfusion lumen (340) and extends to a position at or near perfusion/delivery skive (440) at therapeutic agent delivery segment (240), as shown in FIG. 14. Via skive (440), therapeutic agent delivery lumen (340) of the catheter (150) is in communication with the catheter exterior wall (380) for delivering therapeutic agents to the lumen (18, 30, 40) of a blood vessel (10), as seen in FIGS. 12A and 12B. Thus, the pressure sensing means distal end (702) is in communication with the treatment region (60). In this aspect of the catheter (100) of the present disclosure, there may be provided a two- or three-way valve or check valve (710) in line with the agent delivery lumen (340), the aspiration lumen (320, via aspiration port (520), as shown in FIGS. 16-17), or both, to prevent injection via the aspiration lumen (320), aspiration or backflow via the agent delivery lumen (340), or both (respectively). For the sake of clarity, and to reduce redundancy, the two- or three-way valve or check valve (710) is shown attached to the aspiration port (520). It will be appreciated by those of ordinary skill in the art that such a valve (710) or a plurality thereof may be incorporated to any of the ports (500, 510, 520, 530, 540). As will be appreciated by those of ordinary skill in the art, the catheter (100) may also be constructed so that first pressure sensing means (700) occupies its own separate and dedicated lumen within the catheter (150), and having a proximal opening at pressure sensor connector (550) and distal opening at or near perfusion/delivery skive (440). Between therapeutic agent perfusion aspiration/guidewire/pressure sensor hub (130a) and occluding balloon inflation hub (120), as indicated by FIGS. 15 and 18, the catheter (190) possesses three lumens (300, 320, 340), but may possess a dedicated lumen to house the first pressure sensor (700).

In a related aspect of this embodiment, as shown in FIG. 18, the catheter (100) of the present disclosure may further comprise a second pressure sensing means (704) incorporated into the catheter shaft (190, 192) and hub (130a) of the adapter (110), whereby the pressure of the fluid environment within the therapeutic agent perfusion lumen (340)—at or near the perfusion skive (640), or at any point within the therapeutic agent perfusion lumen (340)—can be known or estimated. In this aspect, the second pressure sensing means (704) may be located alongside the proximal end of the first pressure sensing means (700), with the second pressure sensing means proximal end (705) also located at the pressure sensor connector (550), but with its distal end (706) located within the therapeutic agent perfusion lumen (340) at or near the perfusion skive (640), or at any point within the therapeutic agent perfusion lumen (340). Without intending to be bound to a particular pressure sensor, an example of a pressure sensor suitable for this embodiment is the FOP-MIV (Sequoia Technology, Ltd.; Reading, UK)—a fiber optic pressure sensor. Via the second pressure sensing means (704), a user of the device (100) can know or estimate the pressure experienced by a therapeutic agent at or near the perfusion skive (640). Such information may be particularly relevant for the delivery of such agents as live cell suspensions or other materials that may be susceptible to pressure and/or shear stress. In this embodiment, and as explained above for the example with a first pressure sensing means (700), there may be provided a two- or three-way valve or check valve (710) in line with the agent delivery lumen (340), the aspiration lumen (320, via aspiration port (520), as shown in FIGS. 16-17), or both, to prevent injection via the aspiration lumen (320), aspiration or backflow via the agent delivery lumen (340), or both (respectively).

As illustrated in FIGS. 19A-C, and 25-30, an embodiment of the catheter assembly (105) comprises a catheter (150) extending from a proximal end adapter (110) and longitudinally movable within a vessel (10) along the catheter longitudinal axis (170). Catheter (150) includes elongate catheter shaft (160) having longitudinal axis (170) and defining five lumens therein. At its distal end (140), the catheter assembly (105) has an atraumatic tapered distal tip (200). A distal occluding balloon (210) is located proximal to the tapered distal tip (200) along the longitudinal axis (170) of the catheter (150), a visualization means slot (435) is located proximal to the distal occluding balloon (210) along the longitudinal axis (170) of the catheter (150), and a proximal occluding balloon (250) is located proximal to the visualization means slot (435) along the longitudinal axis (170) of the catheter (150). Between the distal occluding balloon (210) and the visualization means slot (435) is an aspiration segment (220), and between the visualization means slot (435) and the proximal occluding balloon (250) is located an agent delivery segment (240). Each of the aspiration segment (220) and the agent delivery segment (240) have at least one skive port (420 and 440, respectively) formed therein (see also FIGS. 12A and 12B). Proximal end adapter (110) includes balloon inflation/visualization & illumination means hub (125) and delivery hub (130).

Figures 19A, 19B, 19C:
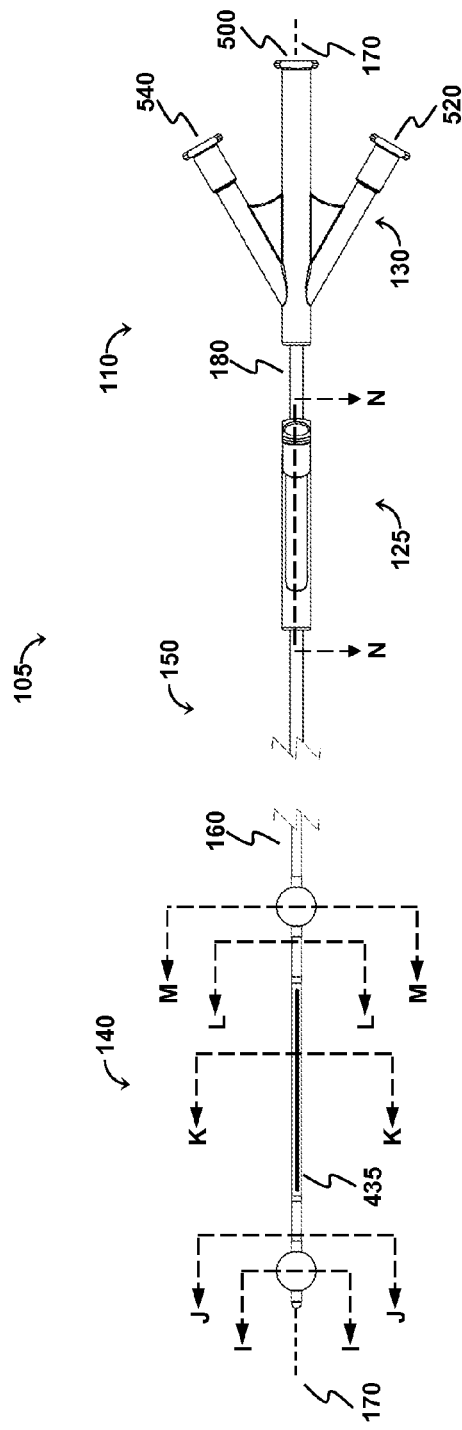
FIG. 19A shows a side devotional view of one embodiment of a catheter of the present disclosure. For clarity, the entire device has not been shown and the figure is not drawn to scale.
FIG. 19B shows a cross-sectional side view of the balloon inflation/visualization hub of the present disclosure, taken along the line N-N, as shown in FIG. 19A. For the sake of clarity, the therapeutic agent perfusion/aspiration and guidewire hub is not shown in this FIG. 19B.
FIG. 19C shows a cross-sectional side view of therapeutic agent perfusion/aspiration and guidewire hub of the present disclosure, along the plane of the page, as shown in FIG. 19A. For the sake of clarity, the balloon inflation/visualization hub is not shown in this FIG. 19C.
Figure 20:
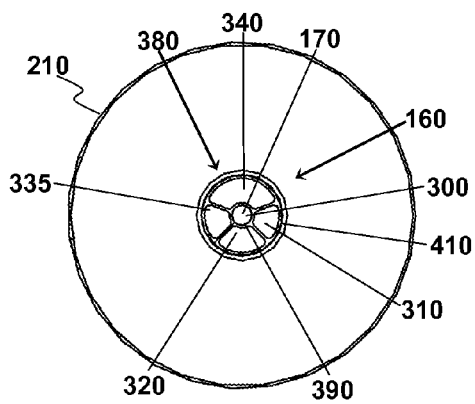
FIG. 20 is a cross-sectional view taken along line B-B as shown in FIG. 19, displaying a distal occluding balloon, five lumens (which may be employed to inflate and deflate balloons, deliver and remove therapeutic agents or biologic samples, or accommodate a visualization means), and a skive port extending through the thickness of the catheter wall such that occluding balloon inflation lumen of the catheter is in communication with the catheter exterior wall for inflating and deflating the distal occluding balloon.
Figure 21:
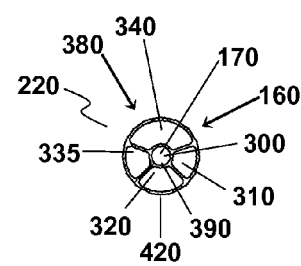
FIG. 21 is a cross-sectional view taken along line C-C as shown in FIG. 19, displaying five lumens (Which may be employed to inflate and deflate balloons, deliver and remove therapeutic agents or biologic samples, or accommodate a visualization means), and an aspiration skive port extending through the thickness of the catheter wall such that aspiration lumen of the catheter is in communication with the catheter exterior wall for aspirating therapeutic agents or fluid samples from the lumen of a blood vessel.
Figure 22:
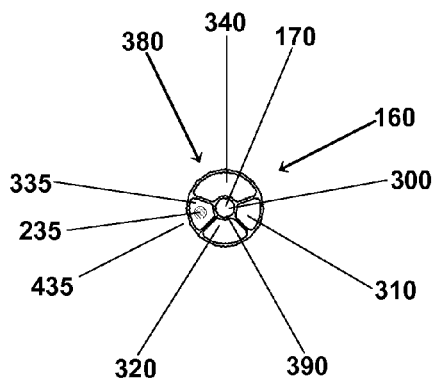
FIG. 22 is a cross-sectional view taken along line D-D as shown in FIG. 19, displaying a space occupying balloon, five lumens (which may be employed to inflate and deflate balloons, deliver and remove therapeutic agents, or accommodate as visualization means), visualization means, and a skive port extending through the thickness of the catheter wall such that the visualization lumen of the catheter is in communication with the catheter exterior wall for visualizing the treatment region.
Figure 24:
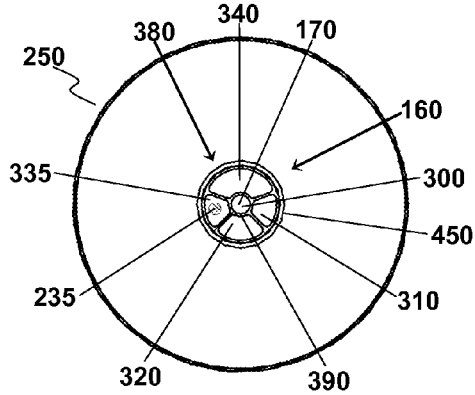
FIG. 24 is a cross-sectional view taken along line F-F as shown in FIG. 19, displaying a proximal occluding balloon, five lumens (which may be employed to inflate and deflate balloons, deliver and remove therapeutic agents, or accommodate a visualization means), a visualization means, and a skive port extending through the thickness of the catheter wall such that occluding balloon inflation lumen of the catheter is in communication with the catheter exterior wall for inflating and deflating the proximal occluding balloon.

As seen in FIGS. 19A-C, 20-24, and 30, balloon inflation/visualization & illumination means hub (125) comprises distal and proximal occluding balloon inflation port (510) and visualization means port (535) (see, e.g., FIG. 19B). Distal and proximal occluding balloon inflation port (510) communicates with distal and proximal occluding balloon inflation lumen (310) via skive port (610), and permits distal and proximal occluding balloons (210 and 250, respectively), discussed below, to be inflated and deflated—in tandem—during use. Visualization means port (535) communicates with visualization means lumen (335) via skive port (635), and permits the visualization means (235), discussed below, to pass through the visualization means lumen (335) to reach and emerge from the visualization means slot (435). The visualization means port (535) may further comprise a valve (710) (e.g., a Tuohy Borst adapter, a two-way, three-way, or check valve, etc.) to prevent backflow via the visualization means lumen (335). The visualization means (235) further comprises output (238), whereby the visualization means (235) may convey information (e.g., to a monitor, a computer, etc.), which may be visualized and/or recorded by means readily available and known in the art.

As seen in FIGS. 19A-C, 20-24, and 30, therapeutic agent perfusion/aspiration and guidewire hub (the "perfusion/aspiration hub," 130) comprises therapeutic agent delivery port (540), therapeutic agent aspiration port (520), and guidewire port (500) (see, e.g., FIG. 19C). Therapeutic agent delivery port (540) communicates with therapeutic agent delivery lumen (340) via skive port (640), and permits delivery of therapeutic agent via skive port (440) to the lumen (18) of a blood vessel (10) e.g., FIGS. 12A & 12B). Therapeutic agent aspiration port (520) communicates with aspiration lumen (320) via skive port (620), and permits aspiration of therapeutic agents or fluid samples via skive port (420) from the lumen (18) of a blood vessel (10) (see, e.g., FIGS. 12A & 12B). Guidewire port (500) is in communication with guidewire lumen (300), which extends the entire length of the catheter (150) to emerge at atraumatic tapered tip (200) as distal opening (202), and permits "over-the-wire" use. As will be appreciated by those of ordinary skill in the art, and as indicated by the jagged line breaks in FIG. 19, the catheter (105) may be either longer or shorter so that the distal end (140) may reach the desired location within a patient while the proximal end adapter (110) remains outside the patient. Between therapeutic agent perfusion/aspiration and guidewire hub (130) and balloon inflation/visualization & illumination means hub (125), the catheter (180) possesses three lumens (300, 320, 340).

Referring now to FIGS. 19A-C, 20, and 25-28, FIG. 20 is a cross-sectional view of the catheter of FIG. 19 taken along line I-I, and illustrates: distal occluding balloon (210); guidewire lumen (300), which communicates with guidewire port (500); distal and proximal occluding balloon inflation lumen (310), which communicates with occlusion balloon inflation port (510) via skive port (610); visualization means lumen (335), which communicates with visualization means port (535) via skive port (635); aspiration lumen (320), which communicates with aspiration port (520) via skive port (620); therapeutic agent delivery lumen (340), which communicates with drug delivery port (540) via skive port (640); and distal occluding balloon inflation skive port (410). Distal occluding balloon inflation skive port (410) extends through the thickness of the catheter exterior wall (380) such that occluding balloon inflation lumen (310) of the catheter (150) is in communication with the catheter exterior wall (380) for inflating the distal occluding balloon (210).

Referring now to FIGS. 19A-C, 21, and 25-28, FIG. 21 is a cross-sectional view of the catheter of FIG. 19 taken along line J-J, and illustrates a cross-sectional view of the therapeutic agent aspiration segment (220), showing: guidewire lumen (300), which communicates with guidewire port (500); distal and proximal occluding balloon inflation lumen (310), which communicates with occlusion balloon inflation port (510) via skive port (610); visualization means lumen 335), which communicates with visualization means port (535) via skive port (635); aspiration lumen (320), which communicates with aspiration port (520) via skive port (620); therapeutic agent delivery lumen (340), which communicates with perfusion port (540) via skive port (640); and aspiration skive port (420). Aspiration skive port (420) extends through the thickness of the catheter exterior wall (380) such that aspiration lumen (320) of the catheter (150) is in communication with the catheter exterior wall (380) for aspirating therapeutic agents or liquid samples from the lumen (18) of a blood vessel (10) (see, e.g., FIGS. 12A and 12B).

Figure 25:
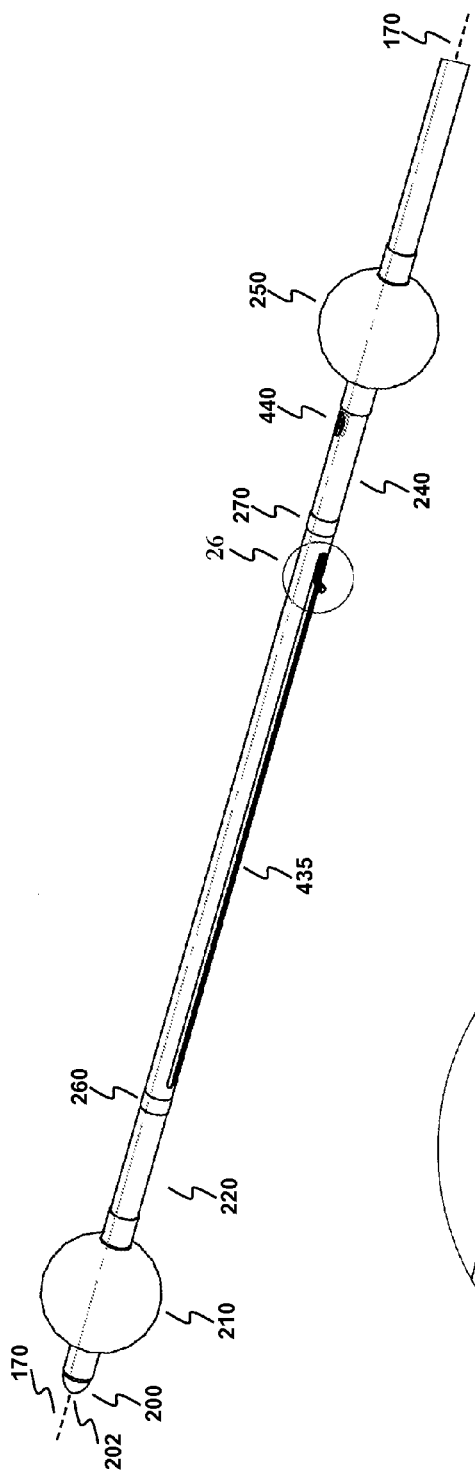
FIG. 25 is a perspective view showing the distal portion of a catheter of the present disclosure with the distal and proximal occluding balloons inflated, the visualization means slot between said balloons, and the visualization means exiting the visualization means slot.
Figure 26:
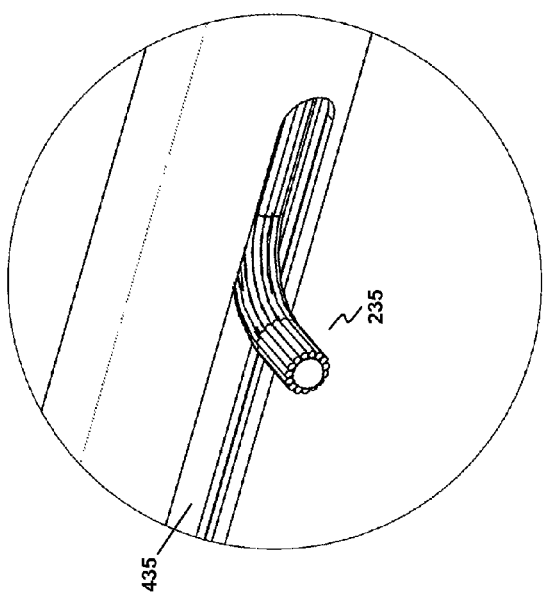
FIG. 26 depicts detail 26, as indicated in FIG. 25, and shows the visualization means exiting the visualization means slot.
Figure 27:
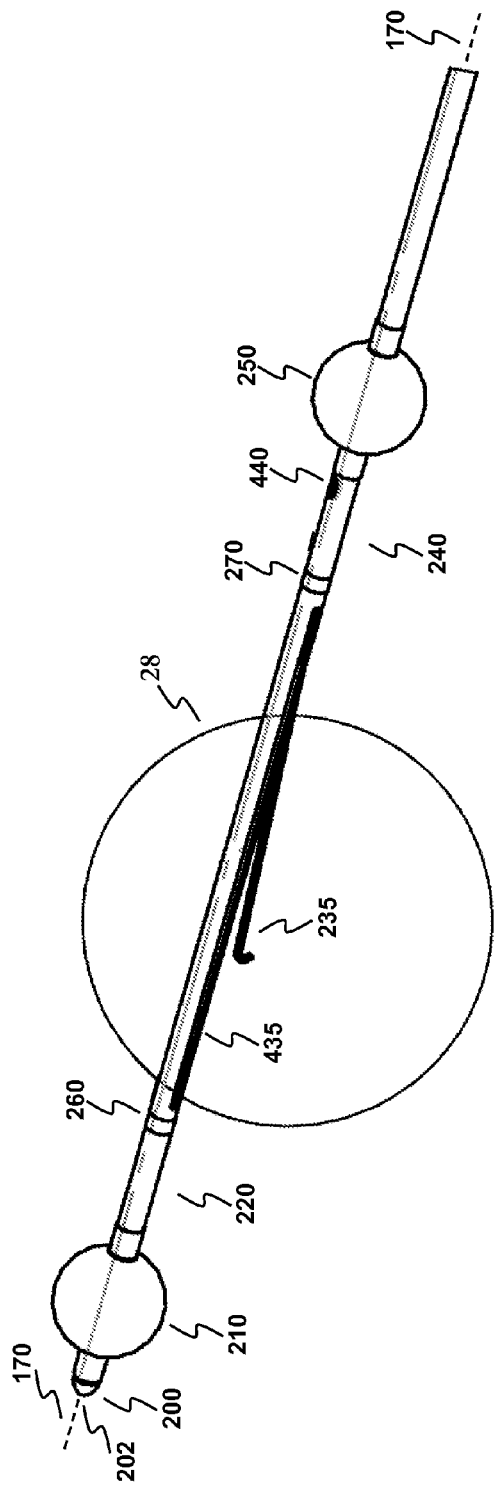
FIG. 27 is a perspective view showing the distal portion of a catheter of the present disclosure with the distal and proximal occluding balloons inflated, the visualization means slot between said balloons, and the visualization means more fully outside the visualization means slot.
Figure 28:
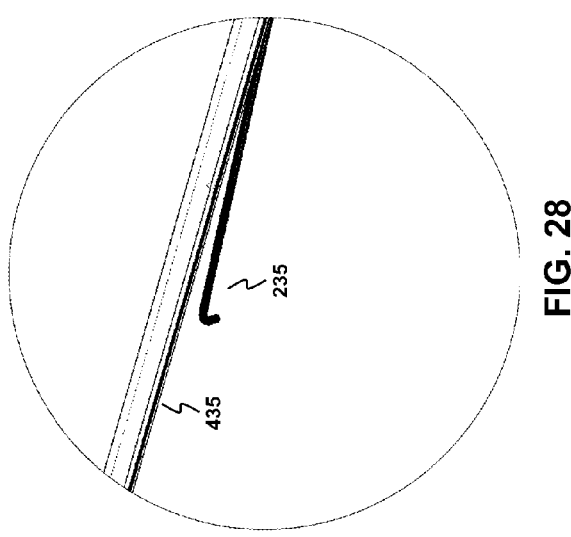
FIG. 28 depicts detail 28, as indicated in FIG. 27, and shows the visualization means more hilly outside the visualization means slot.

Referring now to FIGS. 19A-C, 22, and 25-28, FIG. 22 is a cross-sectional view of the catheter of FIG. 19 taken along line K-K, and illustrates: guidewire lumen (300), which communicates with guidewire port (500); distal and proximal occluding balloon inflation lumen (310), which communicates with occlusion balloon inflation port (510) via skive port (610); visualization means (235) contained within visualization means lumen (335), which communicates with visualization means port (535) via skive port (635); aspiration lumen (320), which communicates with aspiration port (520) via skive port (620); therapeutic agent delivery lumen (340), which communicates with drug delivery port (540) via skive port (640); and space-occupying balloon inflation skive port (430). Visualization means slot (435) extends through the thickness of the catheter exterior wall (380) such that visualization means lumen (335) of the catheter (150) is in communication with the catheter exterior wall (380) for allowing the visualization means (235) to exit the visualization means slot (435) and lumen (335) and enter the lumen (18) of a blood vessel (10). Visualization means slot (435) extends parallel to the longitudinal axis (170) and between aspiration segment (220) and therapeutic agent delivery segment (240) for a length sufficient to allow the visualization means (235) to exit the visualization means slot (435), as shown in FIGS. 27 and 28. By exiting the visualization means slot (435), the visualization means (235) enables visualization of the vessel lumen in a 360° radius (that is, all of the vessel inner wall, without the view being obstructed by the catheter itself).

Referring now to FIGS. 19A-C, 23, and 25-28, FIG. 23 is a cross-sectional view of the catheter of FIG. 19 taken along line L-L, and shows: guidewire lumen (300), which communicates with guidewire port (500); distal and proximal occluding balloon inflation lumen (310), which communicates with occlusion balloon inflation port (510) via skive port (610); visualization means (235) contained within visualization means lumen (335), which communicates with visualization means port (535) via skive port (635); aspiration lumen (320), which communicates with aspiration port (520) via skive port (620); therapeutic agent delivery lumen (340), which communicates with perfusion port (540) via skive port (640); and drug delivery skive port (440). Drug delivery skive port (440) extends through the thickness of the catheter exterior wall (380) such that drug delivery lumen (340) of the catheter (150) is in communication with the catheter exterior wall (380) for delivering therapeutic agents to the lumen (18) of a blood vessel (10) (see, e.g., FIGS. 12A and 12B).

Referring now to FIGS. 19A-C, 24, and 25-28, FIG. 24 is a cross-sectional view of the catheter of FIG. 19 taken along line M-M, and shows: proximal occluding balloon (250); guidewire lumen (300), which communicates with guidewire port (500); distal and proximal occluding balloon inflation lumen (310), which communicates with occlusion balloon inflation port (510) via skive port (610); visualization means (235) contained within visualization means lumen (335), which communicates with visualization means port (535) via skive port (635); aspiration lumen (320), which communicates with aspiration port (520) via skive port (620); therapeutic agent delivery lumen (340), which communicates with drug delivery port (540) via skive port (640); and proximal occluding balloon inflation skive port (450). Proximal occluding balloon inflation skive port (450) extends through the thickness of the catheter exterior wall (380) such that occluding balloon inflation lumen (310) of the catheter (150) is in communication with the catheter exterior wall (380) for inflating the proximal occluding balloon (250).

Referring to FIGS. 20-24, the catheter (160) has a catheter exterior wall (380) and a catheter interior wall (390). As may be appreciated from FIGS. 19A-C, and 20-28, the catheter interior wall (390) defines the guide wire lumen (300). Lumens (335, 340, 310, 320) are peripheral to guidewire lumen (300); they are formed within the catheter (150) and located between the catheter interior wall (390) and the catheter exterior wall (380). The five lumens (300, 310, 340, 335, 320) extend longitudinally through the catheter (150), interconnecting the open proximal end (500, 510, 540, 535, and 520, respectively) with the open distal end (202, 410/450, 440, 435, and 420, respectively).

As seen in FIGS. 19A and 19B, balloon inflation/visualization & illumination means hub (125) is a component of the proximal end adapter (110), lying proximal to the distal end (140) and distal to the therapeutic agent perfusion/aspiration and guidewire hub (130). It will be appreciated by those of ordinary skill in the art that the positions of the balloon inflation/visualization & illumination means hub (125) and the therapeutic agent perfusion/aspiration and guidewire hub (130) may be reversed with respect to one another so that the therapeutic agent perfusion/aspiration and guidewire hub (130) lies between the distal end (140) and the balloon inflation/visualization & illumination means hub (125). The balloon inflation/visualization & illumination means hub (125) is comprised of occlusion balloon inflation port (510), visualization means port (535), and catheter shaft (160). Occlusion balloon inflation port (510) is communicably connected to occlusion balloon inflation lumen (310) of catheter shaft (160) via occlusion balloons hub inflation skive (610). Visualization means port (535) is communicably connected to visualization means lumen (335) of catheter shaft (160) via skive port (635).

As seen in FIGS. 19A and 19C, therapeutic agent perfusion/aspiration and guidewire hub (130) is a component of the proximal end adapter (110), lying proximal to the distal end (140) and proximal to the balloon inflation/visualization & illumination means hub (125). The therapeutic agent perfusion/aspiration and guidewire hub (130) is comprised of therapeutic agent perfusion port (540), aspiration port (520), guidewire port (500), and catheter shaft (160). Therapeutic agent perfusion port (540) is communicably connected to therapeutic agent perfusion lumen (340) of catheter shaft (160) via perfusion hub skive (640). Aspiration port (520) is communicably connected to aspiration lumen (320) of catheter shaft (160) via aspiration hub skive (620). Guidewire port (500) is communicably connected to guidewire lumen (300), which encloses the longitudinal axis (170) of the OVC (105). In the present embodiment, and as shown in FIGS. 20-24, the longitudinal axis (170) is centered within the circular cross-section of the guidewire lumen (300).

FIGS. 25-28 and 12B show the distal and proximal occlusion balloons (210, 250) as they would appear when inflated inside a vessel (10) or other hollow body structure, and show the visualization means (235) as it would appear as it exits the visualization means slot (435). It will be appreciated by those of ordinary skill in the art that occluding balloons (210, 250), visualization means (235), catheter (150, 160), and other components of the device of the present disclosure (105) may be sized appropriately to account for the dimensions that would be required in other hollow body structures (for example, but without intending to be limited, vessels of the lymphatic system, the gastroesophageal tract, the portal-caval system of the liver, the gall bladder and bile ducts, the urinary system, the respiratory system, ducts of the endocrine and exocrine organs, and reproductive organs). Referring to FIG. 25, distal and proximal radio-opaque marker bands (260, 270, respectively) are also shown located on the catheter distal end (140) to facilitate visualization, under fluoroscopic imaging, of the device (105) within a vessel (10). It will be appreciated by those of ordinary skill in the art that radio-opaque markers may also be located upon other portions of the device (105), for example, and without limitation, along the aspiration segment (220), the therapeutic agent delivery segment (240), the occlusion balloons (210, 250), and as described above for the OPC (100). Alternatively, contrast fluid may be used to inflate the occlusion balloons (210, 250), or may be injected through drug delivery skive port (440) or through guidewire lumen (300) to emerge at the distal tapered tip (200) from the opening (202).

Figure 23:
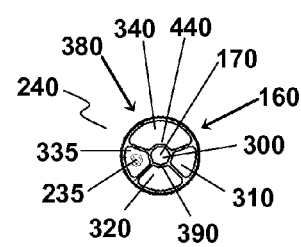
FIG. 23 is a cross-sectional view taken along line E-E as shown in FIG. 19, displaying five lumens which may be employed to inflate and deflate balloons, deliver and remove therapeutic agents, or accommodate a visualization means), a visualization means, and a skive port extending through the thickness of the catheter wall such that therapeutic agent delivery lumen of the catheter is in communication with the catheter exterior wall for delivering therapeutic agents to the lumen of a blood vessel.

As seen in FIGS. 25 and 26, the visualization means (235) may exit the visualization means slot (435) at the slot's most proximal end. The visualization means (235) may, optionally, comprise a bend at its most distal end to facilitate, exit from the visualization means lumen (335) and visualization means slot (435). Referring now to FIGS. 27 and 28, as the visualization means (235) is inserted further distally, along the visualization means lumen (335), the visualization means (235) may further exit the visualization means lumen (335) via the visualization means slot (435) so that the visualization means (235) distal end lies further from the longitudinal axis (170). By allowing the visualization means (235) distal end to depart from the longitudinal axis (170), as shown in FIGS. 27 and 23, and by applying torque to the visualization means (235), the visualization means may turn about the longitudinal axis (170) and so enables visualization of the entire vessel lumen surrounding the device and between the occluding balloons (210, 250). Inflation of the distal occluding balloon (210) and the proximal occluding balloon (250) creates a substantially cylindrical visualization region bounded distally and proximally by the inflated distal and proximal occluding balloons (210 and 250, respectively) and bounded circumferentially by vessel (10), as shown, for example, in FIG. 12A. With only the distal and proximal occluding balloons (210 and 250, respectively) of the device (105) inflated, a relatively large volume remains within the occluded vessel lumen (30), which may advantageously be visualized in its entirety via the visualization means (235).

As shown in FIGS. 20-24, the longitudinal axis (170) is contained within the guide wire lumen (300), but persons having ordinary skill in the art will recognize that the arrangement of lumens may be altered to offset the central lumen (300) from the longitudinal axis (170). Lumens (335, 340, 310, and 320) are formed within the catheter (150) and are located substantially between the catheter exterior wall (380) and the catheter interior wall (390). The lumens (300, 335, 340, 310, and 320) extend longitudinally through the catheter (150), but only guidewire lumen (300) is patent along the entire length of the catheter (150), emerging at the distal tapered tip (200) as opening (202) and so allowing "over-the-wire" use.

In one aspect of this embodiment the catheter (105) may further comprise one or more two- or three-way valves or check valves (710) in fluid communication with the agent delivery lumen (340), the aspiration lumen (320), the visualization means lumen (335) or all three, to prevent injection via the aspiration lumen (320), aspiration or backflow via the agent delivery lumen (340), backflow via the visualization means lumen (335) or all three (respectively). As shown in FIG. 30, a one-way check valve (e.g., a Tuohy-Borst adapter, 710) may be used to prevent backflow via the visualization means lumen (335).

In another aspect of this embodiment, the OVC catheter (105) may include a first pressure sensing means incorporated into the catheter shaft and therapeutic agent perfusion/aspiration/guide wire hub of the adapter (110), as shown and described above for the OPC (100). Without intending to be limited thereby, an example of a suitable pressure sensing means is the FOP-MIV (Sequoia Technology, Ltd.; Reading, UK)—a fiber optic pressure sensor. In a related aspect of this embodiment, the OVC catheter (105) of the present disclosure may further comprise a second pressure sensing means incorporated into the catheter shaft and therapeutic agent perfusion/aspiration/guide wire hub of the adapter (110), as shown and described above for die OPC (100), whereby the pressure of the fluid environment within the therapeutic agent perfusion lumen (340)—at or near the perfusion skive (640), or at any point within the therapeutic agent perfusion lumen (340)—can be known or estimated.

In all embodiments, the catheter (100) can be used with a guide wire (not shown), via guide wire lumen (300), to assist in guiding the catheter (100) to the target segment (60) of the vessel (10). The catheter shafts (150) of the present disclosure are preferably between about 2-7 French units ("Fr." where one French equals ⅓ of a millimeter, or about 0.013 inches). The catheter shafts to be used in coronary arteries are preferably between about 3-5 Fr. in diameter, and most preferably about 3 Fr. The catheter shafts to be used in peripheral vessels are preferably between about 5-8 Fr. in diameter, and most preferably 5 Fr.

The catheter shafts can be made of materials including, but not limited to polymers, natural or synthetic rubber, metal and plastic or combinations thereof, nylon, Pebax, nylon/Pebax blend, Hytrel® and polyethylene. The shaft materials can be selected so as to maximize column strength to the longitudinal length of the shaft. Further, the shaft materials can be braided, so as to provide sufficient column strength. The shaft materials can also be selected so as to allow the device to move smoothly along a guide wire. The catheter (100) can also be provided with a lubricious coating as well as antimicrobial and antithrombogenic coatings, as are known to those of skill in the art. The shaft materials can also be selected so as to maximize bonding of the shaft to the balloon materials. The shaft materials should be selected so as not to interfere with the efficacy of the agent to be delivered or collected. This interference may take the form of absorbing the agent, adhering to the agent or altering the agent in any way, for example.

The balloons can be made of materials including, but not limited to Kraton®, polyurethane, polyolefin or any other biocompatible, elastometric material, or other soft materials. The materials of the balloons may be selected so as to maximize pliability and/or reduce the risk of damage to tissues. The balloon materials should be selected so as not to interfere with the efficacy of the agent to be delivered or collected. Balloon (210, 230, 250) inflation sources can be syringes in communication with lumens (310, 330) via proximal ports (510, 530), or other inflation sources known to those of ordinary skill in the art. The syringes—individually or separately—may contain contrast media or gas or other fluids known to those skilled in the art to be safe and effective for inflating the balloon.

The distal and proximal occlusion balloons (210, 250) used for coronary arteries are preferably 2 to 4 mm in diameter when inflated. The distal and proximal occlusion balloons (210, 250) used for peripheral vessels are preferably 5 to 10 mm in diameter when inflated. The distal and proximal occlusion balloons (210, 250) are preferably about 1 to 2 cm in length, and football-shaped or spherical, or any suitable shape that a compliant to semi-compliant balloon can achieve. The balloons (210, 250) are most preferably about 1 cm long. However, the length and diameter of the balloons can be selected so as to minimize tissue damage. The force exerted against the vessel interior by occlusion balloons (210, 250) is sufficiently great enough to hold the catheter (100) in a stationary position within the vessel or other hollow body structure and provide an adequate seal to control blood or fluid flow. However, the force is not so great as to damage the interior surface of the vessel or other hollow body structure.

Preferably, each occlusion balloon (210, 250) is separated from space occupying balloon (230) by about 1 to 10 mm, or more preferably by about 1 to 7 mm, or most preferably by about 1 to 3 mm. The distance between the most proximal edge of distal occlusion balloon (210) and the most distal edge of space-occupying balloon (230) defines the aspiration segment (220) length; the distance between the most distal edge of proximal occlusion balloon (250) and the most proximal edge of space-occupying balloon (230) defines the therapeutic agent delivery segment (240) length. The aspiration and therapeutic agent delivery segment lengths are preferably about 1 to 10 mm, or more preferably about 1 to 7 mm, or most preferably about 1 to 3 mm.

When using a guide wire, whether the catheter (100) is being used in the coronary arteries or in the peripheral vasculature, the guide wire is preferably about 0.014 to 0.018 inches in diameter.

Therapeutic agents useful with the device of the present disclosure include any one of or a combination of several agents which are gas, liquid, suspensions, emulsions, or solids, which may be delivered or collected from the vessel for therapeutic or diagnostic purposes. Therapeutic agents include biologically active substances, or substances capable of eliciting a biological response, including, but not limited to endogenous substances (growth factors or cytokines, including, but not limited to basic fibroblast growth factor, acidic fibroblast growth factor, vascular endothelial growth factor, angiogenic factors), viral vectors, DNA capable of expressing proteins, sustained release polymers, and unmodified or modified cells. Therapeutic agents can include angiogenic agents which induce the formation of new blood vessels. Therapeutic agents can also include anti-stenosis or anti-restenosis agents which are used to treat the narrowing of blood vessel walls.

The rate of therapeutic agent delivery to the targeted vessel segment (60), as shown in FIGS. 12A and 12B, can be selected so as to minimize tissue damage. The rate of therapeutic agent delivery can depend upon at least the size of perfusion/delivery skive (440) and the pressure under which the agent is passed through the skive (440). The rate of therapeutic agent delivery can be controlled by, for example, an osmotic pump or an infusion pump attached in line with perfusion port (540), perfusion lumen (340), and perfusion skive (440); use of a perfusion pump is also compatible with a two- or three-way valve or check valve appropriately in line with such an arrangement.

Other target spaces that may be accessed by the catheter (100) include but are not limited to any other hollow viscera of the body such as: any of the blood vessels of the cardiovascular system (arteries and veins); vessels of the lymphatic system; the gastroesophageal tract; the portal-caval system of the liver; the gall bladder and bile ducts; the urinary system; the respiratory system; ducts of the endocrine and exocrine organs; and reproductive organs.

The present disclosure also contemplates a method of using balloon occlusion catheters, such as catheter assembly (100), with or without a pressure sensing means (700 and/or 704), and with or without a two- or three-way or check valve (710), for the delivery and/or the collection of agents from a targeted vessel segment (60) in vivo.

The following examples of use are not intended to be an exhaustive list, as those familiar in the art will know many more sub-categories of treatment that keep within the spirit of the disclosure of the device and the method.

EXAMPLE 1

General Steps for Using the OPC

The OPC would be delivered to the treatment site via a minimally invasive insertion technique, over a guidewire, to the treatment area, and the occlusion balloons (210, 250) inflated to isolate the treatment region. Blood and any other fluid trapped between the two inflated occlusion balloons (210, 250) would be aspirated from the treatment region, and the treatment region flushed with saline. The saline would then be aspirated from the treatment region, the space occupying balloon would be inflated, and the agent would be injected into the treatment region. As appropriate, the aspiration lumen could be controlled via die proximal two- or three-way stopcock or check valve to allow the agent to enter the treatment region and prevent the agent from exiling the treatment region prematurely, and further allow selected fluid pressures within the treatment region to be achieved. The space occupying balloon could be optionally deflated, partially, to allow the injection of more agent, whereupon the space occupying balloon would be re-inflated to achieve a greater pressure within the treatment area and to force the agent into the media of the vessel wall. After an appropriate treatment time, the space occupying balloon would be deflated, the agent would be optionally aspirated from the treatment region, and the treatment region optionally flushed (e.g., with saline). Finally, the occlusion balloons would be deflated and the OPC could be withdrawn from the treatment site.

If the lesion being treated is long, or there are multiple lesions present, the OPC can be repositioned and the steps set forth above repeated. As will be clear to those of ordinary skill in the art, the steps set forth herein are susceptible of multiple variations that lie within the scope of the present disclosure (e.g., the space occupying balloon need not be deflated and then re-inflated, or one may elect not to flush the treatment region). The space occupying balloon presents at least two advantages: by taking up space, it decreases the volume of agent required (which is important, given that such agents are generally quite expensive); and it is used to increase pressure within the treatment region, and so push the agent into the media of the vessel wall—the end target of treatment.

EXAMPLE 2

Simultaneous Perfuse in/Drain Out (Simultaneous Exchange of Fluids in the Isolated Volume)

The OPC would be delivered to the treatment site via a minimally invasive insertion technique, over a guidewire, and the occlusion balloons (210, 250) inflated to isolate the treatment region. The space occupying balloon (230) would be inflated to minimize the treatment volume, with the displaced blood draining out through the evacuation lumen (320). Saline could be used as a flushing agent, or the therapeutic agent could be directly injected in through the perfusion lumen (340), displacing the remainder of the blood. Once the treatment region (60) is filled with the therapeutic agent, a stopcock connected to the device (via the evacuation port (520) would be closed, allowing controlled pressure to be built-up in the treatment region with the continued injection of therapeutic agent, resulting in perfusion into the damaged area of the blood vessel/body lumen. Once treatment is complete, the stopcock would be opened, and saline would be injected in through the perfusion lumen (340), flushing the treatment region. The space occupying balloon (230) and the occlusion balloons (210, 250) would then be deflated, allowing movement or removal of the device.

EXAMPLE 3

Two-Part Polymeric Agent/Gel Treatment

This modality allows polymerization at the treatment site. The OPC would be delivered to the treatment site via a minimally invasive insertion technique, over a guidewire, and the occlusion balloons (210, 250) inflated to isolate the treatment region. The space occupying balloon (230) would be inflated to minimize the treatment volume, with the displaced blood draining out through the evacuation lumen (320). The remainder of the blood is aspirated out through the evacuation lumen (320), creating a vacuum in the treatment region. A stopcock attached to the evacuation port (520) would be closed, maintaining the vacuum. Once the treatment region is under vacuum, a two part polymeric agent would be injected into the treatment region—part "A" goes in one port (the perfusion lumen (340) for example), while part "B" goes in through the other (the evacuation lumen (320) for example) so that polymerization takes place in the treatment region. Controlled pressure to be built-up in the treatment region with the continued injection of two-part therapeutic agent, or increasing the pressure of the space occupying balloon, resulting in perfusion/treatment into the damaged area of the blood vessel/body lumen. Once treatment is complete, saline could be injected in through the evacuation lumen (320) while aspiration is facilitated through the perfusion lumen (340), which due to its larger size, would be more appropriate for removal of a polymerized solution or gel, flushing the treatment region. The space occupying balloon (230) and the occlusion balloons (210, 250) would then be deflated, allowing movement or removal of the device. This technique may provide an alternative to therapies that might be too time-consuming if the polymer is too thick to otherwise inject in through the lumens directly.

EXAMPLE 4

Simultaneous Perfuse in/Aspirate Out (Simultaneous Exchange of Fluids in the Treatment Region)

The OPC would be delivered to the treatment site via a minimally invasive insertion technique, over a guidewire, and the occlusion balloons (210, 250) inflated to isolate the treatment region. The space occupying balloon (230) would be inflated to minimize the treatment volume, with the displaced blood draining out through the evacuation lumen (320). Saline could be used as a flushing agent, or the therapeutic agent could be directly injected in through the perfusion lumen (340), while the remainder of the blood is simultaneously aspirated out through the evacuation lumen (320). Once the treatment region is filled with the therapeutic agent, a stopcock connected to the device (via the evacuation port (520) would be closed, allowing controlled pressure to be built-up in the treatment region with the continued injection of therapeutic agent, resulting in perfusion into the damaged area of the body lumen. Once treatment is complete, the stopcock would be opened, and saline would be injected in through the perfusion lumen (340), while aspiration is facilitated through the evacuation lumen (320), flushing the treatment region. The space occupying balloon (230) and the occlusion balloons (210, 250) would then be deflated, allowing movement or removal of the device.

EXAMPLE 5

Sequential Aspirate Out/Perfuse In (Sequential Exchange of Fluids in the Treatment Region)

The OPC would be delivered to the treatment site via a minimally invasive insertion technique, over a guidewire, and the occlusion balloons (210, 250) inflated to isolate the treatment region. The space occupying balloon (230) would be inflated to minimize the treatment volume, with the displaced blood draining out through the evacuation lumen (320). The remainder of the blood is aspirated out through the evacuation lumen (320), creating a vacuum in the treatment region. A stopcock attached to the evacuation port (520) would be closed, maintaining the vacuum. Once the treatment region is under vacuum, therapeutic agent would be injected through the perfusion lumen (340), potentially opening up damaged regions in the intimae for more effective treatment. Controlled pressure to be built-up in the treatment region with the continued injection of therapeutic agent, resulting in perfusion into the damaged area of the blood vessel/body lumen. Once treatment is complete, the stopcock would be opened, and saline would be injected in through the perfusion lumen (340), while aspiration is facilitated through the evacuation lumen (320), flushing the treatment region. The space occupying balloon (230) and the occlusion balloons (210, 250) would then be deflated, allowing movement or removal of the device.

EXAMPLE 6

Perfuse into the treatment region using one of the techniques described above and utilize the space occupying balloon to deploy a stent-graft, trapping the agent between the stent-graft & intimae. This technique would delay the inflation of the space occupying balloon (230) until the therapeutic agent has filled the volume of the treatment region.

EXAMPLE 7

General Steps for Using the OVC

The OVC would be delivered to the treatment site via a minimally invasive insertion technique, over a guidewire, to the treatment area, and the occlusion balloons (210, 250) inflated to isolate the treatment region. Blood and any other fluid trapped between the two inflated occlusion balloons (210, 250) would be aspirated from the treatment region, and the treatment region flushed with saline. Optionally, saline could remain within the treatment region to facilitate visualization. The visualization means (235) would be inserted into the visualization lumen (335), permitting visualization of the treatment region. If present, the saline could be aspirated and the occlusion balloons deflated. Then, the OVC could be repositioned or removed. The visualization means (235) could be removed from die visualization lumen (335) at the user's convenience (e.g., between repositioning steps, at completion of the procedure, etc.).

The OVC may also be used as an agent-delivery catheter, wherein the steps fix delivering an agent would be the same as for the OPC, but without the steps involving the space-occupying balloon. Pressure to push the agent into the media of the vessel wall could be applied via the agent delivery lumen (340).

For the reader's convenience, the following TABLE is provided, listing the enumerated elements described above:

| No. | Description |
|---|---|
| 10 | Blood Vessel |
| 20 | Lumen |
| 30 | Occluded vessel lumen |
| 40 | Occluded vessel lumen |
| 50 | Vessel endothelium |
| 60 | Targeted vessel segment |
| 100 | Occlusion Perfusion Catheter (OPC) |
| 105 | Occlusion Visualization Catheter (OVC) |
| 110 | Proximal End Adapter |
| 120 | Balloon inflation hub |
| 125 | Balloon inflation/visualization & illumination means hub |
| 130 | Therapeutic agent perfusion/aspiration/guide wire hub |
| 130a | Therapeutic agent perfusion/aspiration/guide wire/pressure sensor hub |
| 140 | Distal End |
| 150 | Catheter |
| 160 | 5-lumen extruded catheter shaft |
| 170 | Longitudinal Axis |
| 180 | 3-Lumen catheter shaft between hubs (120) and (130) |
| 190 | 3-Lumen catheter shaft between hubs (120) and (130), with sensor |
| 192 | 5-lumen extruded catheter shaft, with sensor |
| 200 | Atraumatic tapered tip |
| 202 | Distal opening |
| 210 | Distal occlusion balloon |
| 220 | Aspiration segment |
| 230 | Space occupying balloon |
| 235 | Visualization & illumination means |
| 238 | Output |
| 240 | Therapeutic agent delivery segment |
| 250 | Proximal occlusion balloon |
| 260 | Distal marker band |
| 270 | Proximal marker band |
| 300 | Guide wire lumen |
| 310 | Occlusion balloon inflation lumen |
| 320 | Aspiration lumen (evacuates defined volume) |
| 330 | Space occupying balloon inflation lumen |
| 335 | Visualization/illumination lumen |
| 340 | Therapeutic agent perfusion lumen (fills defined treatment volume) |
| 380 | Catheter exterior wall |
| 390 | Catheter interior wall |
| 410 | Distal occlusion balloon inflation skive (catheter distal end) |
| 420 | Aspiration (evacuate) skive (catheter distal end) |
| 430 | Space occupying balloon inflation skive (catheter distal end) |
| 435 | Visualization/illumination means slot |
| 440 | Perfusion (delivery) skive (catheter distal end) |
| 450 | Proximal occlusion balloon inflation skive (catheter distal end) |
| 500 | Guide wire port |
| 510 | Occlusion balloon inflation port (inflates both proximal & distal) |
| 520 | Aspiration (evacuation) port |
| 530 | Space occupying balloon inflation port |
| 535 | Visualization means port |
| 540 | Therapeutic agent delivery (perfusion/fill) port |
| 550 | Fiber optic pressure sensor connector |
| 610 | Occlusion balloons hub inflation skive (catheter proximal end) |
| 620 | Aspiration (evacuation) hub skive (catheter proximal end) |
| 630 | Space occupying balloon hub inflation skive (catheter proximal end) |
| 635 | Visualization & illumination means hub skive |
| 640 | Perfusion (fill) hub skive (catheter proximal end) |
| 700 | First fiber optic pressure sensor |
| 701 | First fiber optic pressure sensor proximal end |
| 702 | First fiber optic pressure sensor distal end |
| 704 | Second fiber optic pressure sensor |
| 705 | Second fiber optic pressure sensor proximal end |
| 706 | Second fiber optic pressure sensor distal end |
| 710 | Two- or three-way valve or check valve |

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue or prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

We claim:
1. A catheter comprising:
 a) a catheter shaft having a longitudinal axis, a distal end having a shaft distal tip, and a proximal end;
 b) a first balloon positioned on the shaft proximal to the shaft distal tip;
 c) a second balloon positioned on the shaft proximal to the first balloon, wherein said second balloon is constructed of a non-compliant material;
 d) a third balloon positioned on the shaft proximal to the second balloon;
 e) an agent delivery segment positioned on the shaft between the first and third balloons and having one agent delivery segment orifice formed therein;
 f) an aspiration segment positioned on the shaft between the first and third balloons and having one aspiration segment orifice formed therein; and
 g) a guidewire lumen formed within the shaft and in communication with: an opening formed in a proximal end of the catheter; and an opening formed in a distal end of the catheter,
 h) an agent delivery lumen in fluid communication with said agent delivery segment orifice; and
 i) a first pressure-sensing means having proximal and distal ends and a length therebetween extending through said agent delivery lumen,
wherein said first pressure sensing means distal end is at the agent delivery segment orifice or within the agent delivery lumen, and wherein said agent delivery segment orifice and said aspiration segment orifice lie on opposite sides of said longitudinal axis.

2. The catheter of claim 1, wherein said first pressure-sensing means proximal end is in communication with a connector formed on the proximal end of the catheter shaft.

3. The catheter of claim 1, further comprising a first inflation lumen in communication with the first and third balloons.

4. The catheter of claim 3, wherein said first inflation lumen is further in communication with a first balloon inflation port formed on the proximal end of the catheter shaft.

5. The catheter of claim 1, further comprising a second inflation lumen in communication with the second balloon.

6. The catheter of claim 5, wherein said second inflation lumen is further in communication with a second balloon inflation port formed on the proximal end of the catheter shaft.

7. The catheter of claim 1, further comprising an aspiration lumen in communication with the aspiration segment orifice.

8. The catheter of claim 7, wherein said aspiration lumen is further in communication with an aspiration port formed on the proximal end of the catheter shaft.

9. The catheter of claim 8, further comprising a valve in communication with said aspiration port.

10. The catheter of claim 1, further comprising an agent delivery lumen in communication with the agent delivery segment orifice.

11. The catheter of claim 10, wherein said agent delivery lumen is further in communication with an agent delivery port formed on the proximal end of the catheter shaft.

12. The catheter of claim 10, further comprising a first pressure-sensing means having proximal and distal ends and a length therebetween extending through said agent delivery lumen, wherein said first pressure-sensing means proximal end is in communication with a connector formed on the proximal end of the catheter shaft and said first pressure-sensing means distal end is at the agent delivery segment orifice or within the agent delivery lumen.

13. The catheter of claim 12, further comprising a second pressure-sensing means having proximal and distal ends and a length therebetween extending through said agent delivery lumen, wherein said second pressure-sensing means proximal end is in communication with the connector formed on the proximal end of the catheter shaft and said second pressure-sensing means distal end is located within the agent delivery lumen.

14. A catheter comprising:
 a) a catheter shaft having a longitudinal axis, a distal end having a shaft distal tip, and a proximal end;
 b) a first balloon positioned on the shaft proximal to the shaft distal tip, a second balloon positioned on the shaft proximal to the first balloon, and a third balloon positioned on the shaft proximal to the second balloon, wherein said second balloon is constructed of a non-compliant material;
 c) a first inflation lumen in communication with the first and third balloons, wherein said first inflation lumen is further in communication with a first balloon inflation port formed on the proximal end of the catheter shaft;
 d) a second inflation lumen in communication with the second balloon, wherein said second inflation lumen is further in communication with a second balloon inflation port formed on the proximal end of the catheter shaft;
 e) an agent delivery lumen, and an agent delivery segment positioned on the shaft between the second and third balloons and having one agent delivery segment orifice formed therein, wherein the agent delivery lumen is in communication with the agent delivery segment orifice and an agent delivery port formed on the proximal end of the catheter shaft;
 f) an aspiration lumen, and an aspiration segment positioned on the shaft between the first and second balloons and having one aspiration segment orifice formed therein, wherein the aspiration lumen is in communication with the aspiration segment orifice and an aspiration port formed on the proximal end of the catheter shaft, said aspiration port optionally further comprising a valve in communication with the aspiration port;
 g) a guidewire lumen formed within the shaft and in communication with an opening formed in a proximal end of the catheter and an opening formed in a distal end of the catheter;
 h) a first pressure-sensing means having proximal and distal ends and a length therebetween extending through said agent delivery lumen, wherein said first pressure-sensing means proximal end is in communication with a connector formed on the proximal end of the catheter shaft and said first pressure-sensing means distal end is at the agent delivery segment orifice or within the agent delivery lumen; and i) a second pressure-sensing means having proximal and distal ends and a length therebetween, wherein said second pressure-sensing means proximal end is in communication with the connector formed on the proximal end of the catheter shaft and said second pressure-sensing means distal end is located within the agent delivery lumen, wherein said agent delivery segment orifice and said aspiration segment orifice lie on opposite sides of said longitudinal axis.

15. A catheter comprising:
a) a catheter shaft having a longitudinal axis, a distal end having a shaft distal tip, and a proximal end;
b) a first balloon positioned on the shaft proximal to the shaft distal tip;
c) a second balloon positioned on the shaft proximal to the first balloon;
d) an agent delivery segment positioned on the shaft between the first and second balloons and having one agent delivery segment orifice formed therein;
e) an aspiration segment positioned on the shaft between the first and second balloons and having one aspiration segment orifice formed therein;
f) a visualization means lumen in communication with a visualization means slot;
g) a visualization means extending through said visualization means lumen at least to said visualization means slot, wherein said visualization means may turn about the longitudinal axis via torque applied to said visualization means; and
h) a guidewire lumen formed within the shaft and in communication with: an opening formed in a proximal end of the catheter; and an opening formed in a distal end of the catheter, wherein said agent delivery segment orifice and said aspiration segment orifice lie on opposite sides of said longitudinal axis.

16. The catheter of claim 15, further comprising a first inflation lumen in communication with the first and second balloons, wherein said first inflation lumen is further in communication with a first balloon inflation port formed on the proximal end of the catheter shaft.

17. The catheter of claim 15, further comprising a visualization means lumen in communication with a visualization means slot and containing at least a portion of said visualization means.

18. The catheter of claim 15, further comprising an aspiration lumen in communication with the aspiration segment orifice, wherein said aspiration lumen is further in communication with an aspiration port formed on the proximal end of the catheter shaft.

19. The catheter of claim 15, further comprising an agent delivery lumen in communication with the agent delivery segment orifice wherein said agent delivery lumen is further in communication with an agent delivery port formed on the proximal end of the catheter shaft.

* * * * *